(12) United States Patent
Jhaveri et al.

(10) Patent No.: US 8,790,889 B2
(45) Date of Patent: Jul. 29, 2014

(54) NEURONAL STIMULATION

(75) Inventors: Dhanisha Jhaveri, Moggill (AU); Perry Francis Bartlett, St. Lucia (AU)

(73) Assignee: The University of Queensland, Brisbane, Queensland (AU)

( * ) Notice: Subject to any disclaimer, the term of this patent is extended or adjusted under 35 U.S.C. 154(b) by 0 days.

(21) Appl. No.: 13/518,234

(22) PCT Filed: Dec. 21, 2010

(86) PCT No.: PCT/AU2010/001721
§ 371 (c)(1),
(2), (4) Date: Aug. 29, 2012

(87) PCT Pub. No.: WO2011/075777
PCT Pub. Date: Jun. 30, 2011

(65) Prior Publication Data
US 2013/0004984 A1    Jan. 3, 2013

(30) Foreign Application Priority Data

Dec. 21, 2009   (AU) .............................. 2009906200

(51) Int. Cl.
*C12Q 1/02*   (2006.01)
*C12N 5/00*   (2006.01)

(52) U.S. Cl.
USPC ........................................... 435/29; 435/325

(58) Field of Classification Search
None
See application file for complete search history.

(56) References Cited

U.S. PATENT DOCUMENTS

| | | | |
|---|---|---|---|
| 5,627,200 | A | 5/1997 | Kreutter et al. |
| 5,786,356 | A | 7/1998 | Bell et al. |
| 5,808,080 | A | 9/1998 | Bell et al. |
| 7,041,438 | B2 | 5/2006 | Carpenter et al. |
| 7,041,684 | B2 | 5/2006 | Rito et al. |
| 7,105,150 | B2 | 9/2006 | Buck et al. |
| 7,115,418 | B2 | 10/2006 | Weiss et al. |
| 2003/0212063 | A1 | 11/2003 | Lafontaine et al. |
| 2004/0034070 | A1 | 2/2004 | Barzaghi et al. |

FOREIGN PATENT DOCUMENTS

| | | |
|---|---|---|
| WO | WO2008/124872 | 10/2008 |
| WO | WO 2009/137874 | 11/2009 |
| WO | WO2011/075777 | 6/2011 |

OTHER PUBLICATIONS

Jhaveri et al. (Norepinephrine Directly Activates Adult Hippocampal Precursors via B3-Adrenergic Receptors. Journal of Neuroscience. Feb. 17, 2010. 30(7):2795-2806).*
Basak, O., and Taylor, V., "Identification of self-replicating multipotent progenitors in the embryonic nervous system by high Notch activity and Hes5 expression," European Journal of Neuroscience. vol. 25 pp. 1006-1022 (2007).
Brezun, J.M., and Daszuta, A., "Depletion in Serotonin Decreases Neurogenesis in the Dentate Gyrus and the Subventricular Zone of Adult Rats," Neuroscience. vol. 89, No. 4 pp. 999-1002 (1999).
Brezun, J.M., and Daszuta, A., "Serotonergic Reinnervation Reverses Lesion-Induced Decreases in PSA-NCAM Labeling and Proliferation of Hippocampal Cells in Adult Rats," Hippocampus. vol. 10 pp. 37-46 (2000).
Charney, "Monoamine Dysfunction and the Pathophysiology and Treatment of Depression," Journal of Clinical Psychiatry. vol. 59, Suppl. 14 pp. 11-14 (1998).
Čikoš et al., "Expression of Beta Adrenergic Receptors in Mouse Oocytes and Preimplantation Embryos," Molecular Reproduction and Development. vol. 71 pp. 145-153 (2005).
Claustre et al., "Effects of the $β_3$-Adrenoceptor (Adrb3) Agonist SR58611A (Amibegron) on Serotonergic and Noradrenergic Transmission in the Rodent: Relevance to Its Antidepressant/Anxiolytic-Like Profile," Neuroscience. vol. 156 pp. 353-364 (2008).
Consoli et al., "Behavioral effects of the $β_3$ adrenoceptor agonist SR58611a: Is it the putative prototype of a new class of antidepressant/anxiolytic drugs?" European Journal of Pharmacology. vol. 573 pp. 139-147 (2007).
Evans et al., "Alternative splicing generates two isoforms of the $β_3$-adrenoceptor which are differentially expressed in mouse tissues," British Journal of Pharmacology. vol. 127, No. 6 pp. 1525-1531 (1999).
Ge et al., "GABA regulates synaptic integration of newly generated neurons in the adult brain," Nature. vol. 439 pp. 589-593 (2006).
Ge et al., "GABA sets the tempo for activity-dependent adult neurogenesis," Trends in Neurosciences. vol. 30, No. 1 pp. 1-8 (2007).
Greenberg, M.E., and Ziff, E.B., "Stimulation of 3T3 cells induces transcription of the *c-fos* proto-oncogene," Nature. vol. 311, No. 5985 pp. 433-438 (1984).
Hagg, "From Neurotransmitters to Neurotrophic Factors to Neurogenesis," Neuroscientist. vol. 15, No. 1 pp. 20-27 (2009).
Huang, G., and Herbert, J., "Stimulation of Neurogenesis in the Hippocampus of the Adult Rat by Fluoxetine Requires Rhythmic Change in Corticosterone," Biological Psychiatry. vol. 59, No. 7 pp. 619-624 (2006).
Hyttel, "Phamacological characterization of selective serotonin reuptake inhibitors (SSRIs)," International Clinical Psychopharmacology. vol. 9, Suppl. 1 pp. 19-26 (1994).
Kageyama et al., "Roles of bHLH genes in neural stem cell differentiation," Experimental Cell Research. vol. 306 pp. 343-348 (2005).
Kempermann et al., "Milestones of neuronal development in the adult hippocampus," Trends in Neurosciences. vol. 27, No. 8 pp. 447-452 (2004).
Liu et al., "Identification of Small-Molecule Modulators of Mouse SVZ Progenitor Cell Proliferation and Differentiation Through High-Throughput Screening," Journal of Biomolecular Screening: vol. 14, No. 4 pp. 319-329 (2009).
Lledo et al., "Adult neurogenesis and functional plasticity in neuronal circuits," Nature Reviews Neuroscience. vol. 7 pp. 179-193 (2006).
Nácher et al., "*N*-Methyl-D-Aspartate Receptor Expression During Adult Neurogenesis in the Rat Dentate Gyrus," Neuroscience. vol. 144, No. 3 pp. 855-864 (2007).

(Continued)

*Primary Examiner* — Karen Cochrane Carlson
*Assistant Examiner* — Natalie Moss
(74) *Attorney, Agent, or Firm* — Jenkins, Wilson, Taylor & Hunt, P.A.

(57) ABSTRACT

A method of activating a latent neural precursor cell population, comprising: (1) providing a neural cell population derived from the hippocampus; (2) introducing the neural cell population to a neurosphere-forming culture medium; and (3) activating the latent precursor cell population by treatment with a β3 adrenergic receptor agonist.

4 Claims, 12 Drawing Sheets

(56) References Cited

OTHER PUBLICATIONS

Simiand et al., "Antidepressant profile in rodents of SR 58611A, a new selective agonist for atypical β-adrenoceptors," European Journal of Pharmacology. vol. 219, No. 2 pp. 193-201 (1992).

Strosberg, "Association of $\beta_3$-adrenoceptor polymorphism with obesity and diabetes: current status," TRENDS in Pharmacological Sciences. vol. 18, No. 12 pp. 449-454 (1997).

Bull, N.D., and Bartlett, P.F., "The Adult Mouse Hippocampal Progenitor Is Neurogenic But Not a Stem Cell," The Journal of Neuroscience. vol. 25, No. 47 pp. 10815-10821 (2005).

Counts, S.E., and Mufson, E.J., "Noradrenaline activation of neurotrophic pathways protects against neuronal amyloid toxicity," Journal of Neurochemistry. vol. 113, No. 3 pp. 649-660 (2010).

Cryan et al., "Norepinephrine-deficient mice lack responses to antidepressant drugs, including selective serotonin reuptake inhibitors," PNAS. vol. 101, No. 21 pp. 8186-8191 (2004).

David et al., "Neurogenesis-Dependent and—Independent Effects of Fluoxetine in an Animal Model of Anxiety/Depression," Neuron. vol. 62 pp. 479-493 (2009).

Deisseroth et al., "Excitation-Neurogenesis Coupling in Adult Neural Stem/Progenitor Cells," Neuron. vol. 42 pp. 535-552 (2004).

Gould, "Serotonin and Hippocampal Neurogenesis," Neuropsychopharmacology. vol. 21, No. 2S pp. 46S-51S (1999).

International Search Report corresponding to International Patent Application No. PCT/AU2010/001721 dated Mar. 29, 2011.

Jha et al., "Selective serotonin depletion does not regulate hippocampal neurogenesis in the adult rat brain: Differential effects of *p*-chlorophenylalanine and 5,7-dihydroxytryptamine," Brain Research. vol. 1075 pp. 48-59 (2006).

Jhaveri et al., "Norephinephrine Directly Activates Adult Hippocampal Precursors via $\beta_3$-Adrenergic Receptors," The Journal of Neuroscience. vol. 30, No. 7 pp. 2795-2806 (2010).

Kulkarni et al., "Depletion of norepinephrine decreases the proliferation, but does not influence the survival and differentiation, of granule cell progenitors in the adult rat hippocampus," European Journal of Neuroscience. vol. 16, No. 10 pp. 2008-2012 (2002).

Malberg, J.E., and Duman, R.S., "Cell Proliferation in Adult Hippocampus is Decreased by Inescapable Stress: Reversal by Fluoxetine Treatment," Neuropsychopharmacology. vol. 28 pp. 1562-1571 (2003).

Malberg et al., "Chronic Antidepressant Treatment Increases Neurogenesis in Adult Rat Hippocampus," The Journal of Neuroscience. vol. 20, No. 24 pp. 9104-9110 (2000).

Ming, G.L., and Song, H., "Adult Neurogenesis in the Mammalian Central Nervous System," Annual Review of Neuroscience. vol. 28 pp. 223-250 (2005).

Notification Concerning Transmittal of International Preliminary Report on Patentability (Chapter I of the Patent Cooperation Treaty) corresponding to International Patent Application No. PCT/AU2010/001721 dated Jul. 5, 2012.

Ohtsuka et al., "Visualization of embryonic neural stem cells using Hes promoters in transgenic mice," Molecular and Cellular Neuroscience. vol. 31 pp. 109-122 (2006).

Overstreet et al., "Confirmation of antidepressant potential of the selective β3 adrenoceptor agonist amibegron in an animal model of depression," Pharmacology, Biochemistry and Behavior. vol. 89, No. 4 pp. 623-626 (2008).

Stemmelin et al., "Stimulation of the $\beta_3$-Adrenoceptor as a Novel Treatment Strategy for Anxiety and Depressive Disorders," Neuropsychopharmacology. vol. 33 pp. 574-587 (2008).

Summers et al., "Expression of $\beta_3$-adrenoceptor mRNA in rat brain," British Journal of Pharmacology. vol. 116 pp. 2547-2548 (1995).

Tashiro et al., "NMDA-receptor-mediated, cell-specific integration of new neurons in adult dentate gyrus," Nature. vol. 442 pp. 929-933 (2006).

Vaidya et al., "Neurotransmitter Regulation of Adult Neurogenesis: Putative Therapeutic Targets," CNS & Neurological Disorders—Drug Targets. vol. 6, No. 5 pp. 358-374 (2007).

Vollmayr et al., "Neurogenesis and depression: what animal models tell us about the link," European Archives of Psychiatry and Clinical Neuroscience. vol. 257, No. 5 pp. 300-303. (2007).

Walker et al., "Latent Stem and Progenitor Cells in the Hippocampus Are Activated by Neural Excitation," The Journal of Neuroscience. vol. 28, No. 20 pp. 5240-5247 (2008).

Wang et al., "Chronic Fluoxetine Stimulates Maturation and Synaptic Plasticity of Adult-Born Hippocampal Granule Cells," The Journal of Neuroscience. vol. 28, No. 6 pp. 1374-1384 (2008).

Written Opinon of the International Searching Authority corresponding to International Patent Application No. PCT/AU2010/001721 dated Mar. 29, 2011.

Zhao et al., "Mechanisms and Functional Implications of Adult Neurogenesis," Cell. vol. 132 pp. 645-660 (2008).

Bull, N.D., and Bartlett, P.F., "The Adult Mouse Hippocampal Progenitor Is Neurogenic But Not a Stem Cell," The Journal of Neuroscience. vol. 25, No. 47 pgs. 10815-10821 (2005).

Counts, S.E., and Mufson, E.J., "Noradrenaline activation of neurotrophic pathways protects against neuronal amyloid toxicity," Journal of Neurochemistry. vol. 113, No. 3 pgs. 649-660 (2010).

Cryan et al., "Norepinephrine-deficient mice lack responses to antidepressant drugs, including selective serotonin reuptake inhibitors," PNAS. vol. 101, No. 21 pgs. 8186-8191 (2004).

David et al., "Neurogenesis-Dependent and -Independent Effects of Fluoxetine in an Animal Model of Anxiety/Depression," Neuron. vol. 62 pgs. 479-493 (2009).

Deisseroth et al., "Excitation-Neurogenesis Coupling in Adult Neural Stem/Progenitor Cells," Neuron. vol. 42 pgs. 535-552 (2004).

Gould, "Serotonin and Hippocampal Neurogenesis," Neuropsychopharmacology. vol. 21, No. 2S pgs. 46S-51S (1999).

Jha et al., "Selective serotonin depletion does not regulate hippocampal neurogenesis in the adult rat brain: Differential effects of *p*-chlorophenylalanine and 5,7-dihydroxytryptamine," Brain Research. vol. 1075 pgs. 48-59 (2006).

Jhaveri et al., "Norephinephrine Directly Activates Adult Hippocampal Precursors via $\beta_3$-Adrenergic Receptors," The Journal of Neuroscience. vol. 30, No. 7 pgs. 2795-2806 (2010).

Kulkarni et al., "Depletion of norepinephrine decreases the proliferation, but does not influence the survival and differentiation, of granule cell progenitors in the adult rat hippocampus," European Journal of Neuroscience. vol. 16, No. 10 pgs. 2008-2012 (2002).

Malberg, J.E., and Duman, R.S., "Cell Proliferation in Adult Hippocampus is Decreased by Inescapable Stress: Reversal by Fluoxetine Treatment," Neuropsychopharmacology. vol. 28 pgs. 1562-1571 (2003).

Malberg et al., "Chronic Antidepressant Treatment Increases Neurogenesis in Adult Rat Hippocampus," The Journal of Neuroscience. vol. 20, No. 24 pgs. 9104-9110 (2000).

Ming, G.L., and Song, H., "Adult Neurogenesis in the Mammalian Central Nervous System," Annual Review of Neuroscience. vol. 28 pgs. 223-250 (2005).

Notification Concerning Transmittal of Copy of International Preliminary Report on Patentability (Chapter I of the Patent Cooperation Treaty) corresponding to International Patent Application No. PCT/AU2010/001721 dated Jul. 5, 2012.

Ohtsuka et al., "Visualization of embryonic neural stem cells using Hes promoters in transgenic mice," Molecular and Cellular Neuroscience. vol. 31 pgs. 109-122 (2006).

Overstreet et al., "Confirmation of antidepressant potential of the selective β3 adrenoceptor agonist amibegron in an animal model of depression," Pharmacology, Biochemistry and Behavior. vol. 89, No. 4 pgs. 623-626 (2008).

Stemmelin et al., "Stimulation of the $\beta_3$-Adrenoceptor as a Novel Treatment Strategy for Anxiety and Depressive Disorders," Neuropsychopharmacology. vol. 33 pgs. 574-587 (2008).

Summers et al., "Expression of $\beta_3$-adrenoceptor mRNA in rat brain," British Journal of Pharmacology. vol. 116 pgs. 2547-2548 (1995).

Tashiro et al., "NMDA-receptor-mediated, cell-specific integration of new neurons in adult dentate gyrus," Nature. vol. 442 pgs. 929-933 (2006).

(56) References Cited

OTHER PUBLICATIONS

Vaidya et al., "Neurotransmitter Regulation of Adult Neurogenesis: Putative Therapeutic Targets," CNS & Neurological Disorders—Drug Targets. vol. 6, No. 5 pgs. 358-374 (2007).

Vollmayr et al., "Neurogenesis and depression: what animal models tell us about the link," European Archives of Psychiatry and Clinical Neuroscience. vol. 257, No. 5 pgs. 300-303 (2007).

Walker et al., "Latent Stem and Progenitor Cells in the Hippocampus Are Activated by Neural Excitation," The Journal of Neuroscience. vol. 28, No. 20 pgs. 5240-5247 (2008).

Wang et al., "Chronic Fluoxetine Stimulates Maturation and Synaptic Plasticity of Adult-Born Hippocampal Granule Cells," The Journal of Neuroscience. vol. 28, No. 6 pgs. 1374-1384 (2008).

Zhao et al., "Mechanisms and Functional Implications of Adult Neurogenesis," Cell. vol. 132 pgs. 645-660 (2008).

* cited by examiner

NEURONAL STIMULATION

TECHNICAL FIELD

The present invention relates to latent neural precursor cells capable of direct activation by a β3 adrenergic receptor agonist, in particular, norepinephrine, and to the use of these latent neural precursor cells in screening candidate pharmaceuticals. The invention also relates to a neural cell population derived by activation of said latent neural precursor cells, cell cultures containing same and the use thereof in medical treatment. Further, the present invention relates to the use of β3-adrenergic receptors in screening candidate pharmaceuticals.

BACKGROUND ART

Many neurological diseases such as dementia, including Alzheimer's disease, stroke, depression, Parkinson's disease and motor neuron disease are associated with a reduction in the number of neurons. The decline in number of neurons may be rapid, as in the case of stroke, or slower, as in the case of Alzheimer's disease.

After heart disease and cancer, stroke is the third leading cause of death in western industrialized countries and the major cause of severe, long-term disability in adults with 56% of people following a stroke suffering from a severe or profound disability. There are over 20 million stroke survivors worldwide. This ailment represents an economic burden estimated to be $45 billion a year in the US alone and is expected to rise significantly. A significant factor contributing to this trend is the increased susceptibility to stroke among the elderly.

Alzheimer's disease is the most common dementia occurring in the elderly, affecting about 10% of people above 65 years and 40% above 80 years. Alzheimer's is predicted to afflict up to 16 million people by the middle of this century unless a cure or prevention is found in the United States alone. 50-75% of dementia is estimated to be caused by Alzheimer's disease. The prevalence of Alzheimer's disease is slightly higher in women than in men, but almost twice as many women live with dementia because of their longer life expectancy.

Alzheimer's disease is a progressive neurodegenerative disease characterized by memory loss and general cognitive and behavioural decline. Alzheimer's disease is commonly associated with a non-cognitive symptomatology including depression. Histologically, Alzheimer's disease is defined by the presence in post-mortem human brain specimens of amyloid neuritic plaques, the formation of neurofibrillary tangles and degeneration of the cholinergic neurons.

Parkinson's disease is associated with the destruction of neurons, but the damage is restricted to the dopamine-producing cells in the substantia nigra (part of the basal ganglia). The most common symptoms of Parkinson's disease are tremor, rigidity and difficulty initiating movement. In the US alone, some one million patients are affected and 50,000 new patients are added annually.

Depression is one of the most common mental disorders in the community. In Australia one in four women and one in six men will experience depression at some time in their life. Depression presents with depressed mood and loss of interest or pleasure. It affects about 121 million people worldwide.

Motor neuron disease is the name given to a group of diseases in which nerve cells that control the muscles degenerate and die. It is rarely diagnosed in people less than 30 years of age. In Australia, there are around 400 new cases of motor neuron disease each year. There is no effective method of treatment and the disease is generally fatal within 1-5 years of diagnosis. More than one person dies of Motor neuron disease each day in Australia.

There are several regions in the brain where stem cells are known to exist, including the sub-ventricular zone and the hippocampus. It is thought that the stem cells in these areas are already working at maximum capacity to generate new neurons for general "self-maintenance".

The adult mammalian hippocampus harbours neural precursors that reside and proliferate in the milieu of the neurogenic niche (Ming, 2005). These precursors differentiate into neurons that functionally integrate into the hippocampal neurocircuitry, thereby influencing functions such as learning and memory (Lledo, 2006). Elucidating the regulatory mechanisms to enhance this form of cellular plasticity has been a major focus in recent years, driven by the need to combat neurodegenerative disorders such as Alzheimer's disease and stroke, as well as psychiatric diseases including depression.

Accumulating evidence has suggested an important role for synaptic activity in regulating the process of adult hippocampal neurogenesis (Ming, 2005 and Zhao, 2008). Neural excitation has been shown to activate a latent stem cell pool (Walker, 2008), to promote precursors to commit to a neurogenic fate (Deisseroth, 2004), as well as to enhance the survival and integration of newly born neurons in the adult hippocampus (Ge, 2006 and Tashiro, 2006). Amongst the factors that are released following synaptic activity are the neurotransmitters, trophic roles for which are increasingly being appreciated in the regulation of neurogenesis (Hagg, 2009 and Vaidya (2007). Recent studies have shown that glutamate and GABA receptors are present on a subset of adult hippocampal precursors and regulate their proliferation (Ge, 2006, Ge, 2007 and Nacher, 2007). However, their role in directly activating a latent precursor population has been ruled out (Walker, 2008).

Within the monoaminergic neurotransmitter family, a large number of in vivo studies have focused on the roles of serotonin and norepinephrine, revealing a strong correlation between their levels and the extent of hippocampal neurogenesis (Brezun, 1999, Kulkarni, 2002 and Brezun, 2000) Furthermore, impaired neurogenesis has been demonstrated in animal models of stress and depression (Malberg, 2003 and Vollmayr, 2007), where a significant reduction in the levels of serotonin and norepinephrine are also commonly observed (Vaidya, 2007 and Charney, 1998). In agreement with these lines of evidence, pharmacological agents, such as antidepressants that act by elevating levels of serotonin and norepinephrine, have been shown to enhance hippocampal neurogenesis (Malberg, 2000). Similarly, studies utilizing pharmacological lesions have proposed a proliferative role for norepinephrine, although controversy still exists regarding the role of serotonin in regulating the proliferation of hippocampal precursors (Kulkarni, 2002, Jha, 2006 and Huang, 2006). However, one of the limitations of the current in vivo approaches is the inability to dissect out direct versus non-cell-autonomous effects of these neurotransmitters on the precursor population. Whether serotonin or norepinephrine has a direct effect on adult hippocampal precursors, and the cellular and molecular identity of such a precursor population, therefore was hitherto unknown.

SUMMARY OF THE INVENTION

The present inventors have found that adult hippocampal precursors may be activated in vitro by norepinephrine in neurosphere-forming media so as to produce neurospheres. Specifically, they found a direct action of norepinephrine in activating Hes5-expressing stem and precursor cell populations. It is thought that this new source of neurons could play a critical role in the replacement of damaged and lost neurons in neurological diseases where neuron loss is a feature. Furthermore, they found that the effects of norepinephrine are mediated by β3 adrenergic receptors, which are exclusively expressed by this neurogenic precursor pool, hence β3 adrenergic receptor agonists should activate the precursor cell population. Additionally they developed a novel slice-sphere assay and examined the effects of two major classes of widely prescribed antidepressants. In so doing they demonstrated that norepinephrine-selective reuptake inhibitors (NRIs) but not serotonin-selective reuptake inhibitors (SSRIs) significantly enhance hippocampal neural precursor activity, and further established that the method is applicable to screening candidate pharmaceuticals.

In one aspect, the present invention provides a method of activating a latent neural precursor cell population, comprising:

(1) providing a neural cell population derived from the hippocampus;

(2) introducing the neural cell population to a neurosphere-forming culture medium; and (3) activating the latent precursor cell population by treatment with a β3 adrenergic receptor agonist.

A neural cell population in which a latent neural precursor cell population is activated may be isolated. Thus the method may comprise selecting cells which demonstrate the property of self-renewal and multipotency.

Accordingly, in a further aspect the present invention provides a composition comprising an otherwise latent neural precursor cell population which has been activated by treatment with a β3 adrenergic receptor agonist, characterised in that the activated cell population comprises cells which are self-renewing and multipotent, and which are Hes5$^{+ve}$, and a medium capable of supporting the growth of the cells.

The method of the invention may further comprise inducing differentiation and proliferation.

Accordingly, in a further aspect the invention provides a composition comprising a cell population generated from an otherwise latent neural precursor cell population which has been activated by treatment with a β3 adrenergic receptor agonist and in which induction of differentiation and proliferation has been induced, and a medium capable of supporting the growth of the cells.

In particular, the discovery of this latent precursor cell population opens the possibility that the in vivo population can be stimulated to proliferate and differentiate. Therefore the precursor cell population of the present invention is useful as a model for the screening of potential neurologically active therapeutic compounds.

Accordingly, in one aspect of the present invention there is provided a method of screening a potentially neurologically active therapeutic compound comprising the steps of:

(1) providing a neural cell population derived from the hippocampus in which a latent neural precursor cell population capable of activation by treatment with a β3 adrenergic receptor agonist is present;

(2) contacting said neural cell population with at least one candidate pharmaceutical agent; and (3) determining if said candidate agent activates the latent precursor cell population.

Furthermore, the present inventors found that the effects of norepinephrine are mediated by β3 adrenergic receptors, which are exclusively expressed by this neurogenic precursor pool.

Accordingly in a still further aspect of the present invention there is provided a method of screening a potentially neurologically active therapeutic compound comprising the steps of:

(1) providing a β3 adrenergic receptor;

(2) contacting said β3 adrenergic receptor with at least one candidate pharmaceutical agent; and (3) determining if said candidate agent binds to said β3 adrenergic receptor.

The observation that a cell population generated from an otherwise latent neural precursor cell population may be activated by treatment with a β3 adrenergic receptor agonist opens the possibility that an in vivo population can be stimulated to proliferate and differentiate. Thus β3 adrenergic receptor agonists have utility in the treatment of neurodegenerative diseases such as dementia, including Alzheimer's disease, stroke, depression, Parkinson's disease and motor neuron disease through reversal in the reduction in the number of neurons that occurs in these diseases.

Accordingly in a still further aspect of the present invention there is provided a method of treatment of a neurodegenerative disease comprising administering a β3 adrenergic receptor agonist to a patient in need of such treatment.

In a still further aspect of the present invention there is provided the use of a β3 adrenergic receptor agonist in the manufacture of a medicament for the treatment of a neurodegenerative disease.

In a still further aspect the present invention provides the use of a β3 adrenergic receptor agonist in the treatment of a neurodegenerative disease In an embodiment the neurodegenerative disease is selected from the group consisting of dementia, including Alzheimer's disease, stroke, depression, Parkinson's disease and motor neuron disease.

ABBREVIATIONS

Figure 1:
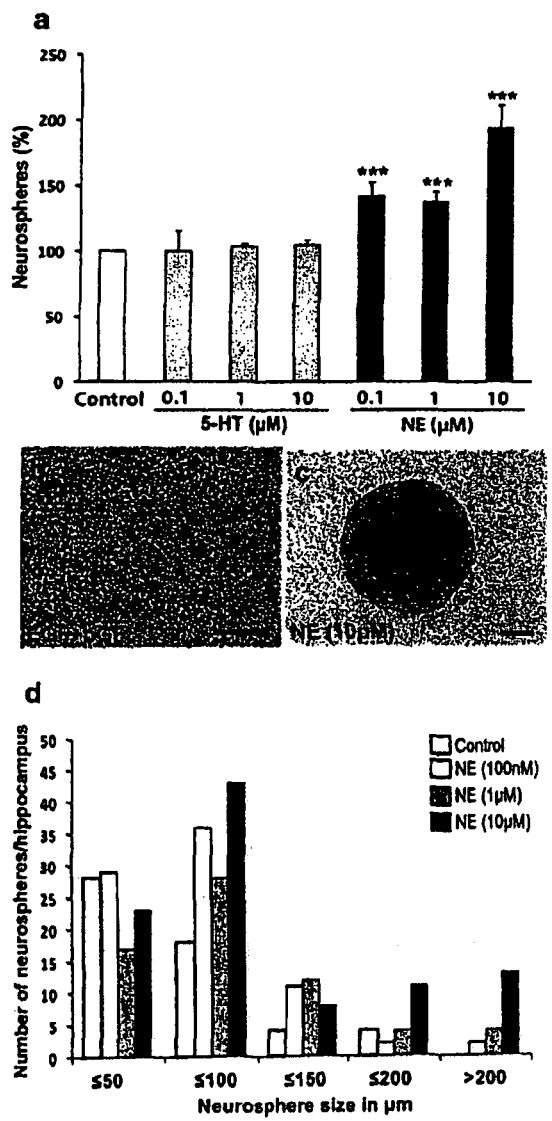
FIG. 1. Norepinephrine but not serotonin activates a precursor cell population from the adult hippocampus. (a) Treatment of adult hippocampal cells with norepinephrine (NE) but not serotonin (5-HT) in the presence of EGF and bFGF, significantly enhanced neurosphere formation with up to a 2-fold increase observed at 10 μM (mean±SEM; n=3; ***p<0.001). In addition, norepinephrine treatment generated a number of very large neurospheres, an example of which is shown in (c) compared to smaller neurospheres generated in the control (b). (d) Distribution of neurospheres, based on size, generated in control conditions and in the presence of increasing concentrations of norepinephrine. Note the emergence of a population of neurospheres measuring more than 200 μm in diameter in the presence of norepinephrine. Scale bars, 100 μm.

BRL37344, sodium 4-(2-[2-hydroxy-3-chlorophenyl}ethylamino]propyl)phenoxyacetate; CGP12177A, (−)-4-(3-tert-butylamino-2-hydroxypropoxy)-benzimidazol-2-one; CGP20712A, 2-hydroxy-5-(2-[{2-hydroxy-3-(4-[1-methyl-4-trifluoromethyl-2-imidazolyl]phenoxy)-propyl}amino]ethoxy)benzamide; CL316243 disodium(R,R)-5-(2-[{2-(3-chlorophenyl)-2-hydroxyethyl}-amino]propyl)-1,3-benzodioxole-2,2,dicarboxylate; ICYP, iodocyanopindolol; I742791, (S)—N-(4-[2-{(3-[4-hydroxyphenoxy]-2-hydroxypropyl)amino}ethyl]phenyl)-4-iodobenzene-sulfonamide; L-755507, 4-[[(Hexylamino)carbonyl]amino]-N-[4-[2S-[[(2-hydroxy-3-(4-hydroxyphenoxy)propyl]amino]ethyl]phenyl]-benzenesulfonamide; L748328, (S)—N-(4-[2-{(3-[3-{aminosulfonyl}phenoxy]-2-hydroxypropyl)-amino}ethyl]phenyl)benzenesulfonamide; RO363, (−)-1-(3,4-dimethoxyphenethylamino)-3-(3,4-dihydroxyphenoxy)-2-propanol)oxalate; SB251023, (4-[1-{2-(S)-hydroxy-3-(4-hydroxyphenoxy)-propyl-amino}cyclopentylmethyl]phenoxymethyl)phenylphosphonic acid lithium salt; SR58611A, N-[(2S)-7-carbethoxymethoxy-1,2,3,4-tetrahydronaphth-2-yl]-(2R)-2-hydroxy-2-(3-chlorophenyl)ethanamine; SR59230A, 3-(2-ethylphenoxy)-1([1s]-1,2,3,4-tetrahydronaphth-1-ylamino)-2S-propanol oxalate; ZD7114, (S)-4-[2-Hydroxy-3-phenoxypropylamino ethoxy]-N-(2-methoxyethyl)phenoxyacetamide.

DETAILED DESCRIPTION OF THE INVENTION

In one aspect, the present invention provides a method of activating a latent neural precursor cell population. The method involves introducing a neural cell population to a neurosphere-forming culture medium and activating the latent precursor cell population by treatment with a β3 adrenergic receptor agonist. The method may further comprise selection of cells that demonstrate the property of self-renewal and multipotency. The activated cell population comprises cells which are self-renewing and multipotent.

Further it has been found that Hes5 acts as a marker for the precursor cells. Thus, in an embodiment, Hes5 may be selected for in seeking to isolate or enrich for the precursor cells. Upon co-labelling with known stem/precursor cell markers, it was found that 39% of the Hes5$^{+ve}$ cells expressed GFAP, a marker for quiescent neural precursor or neural stem-like cells. Accordingly, in an embodiment the precursor cells are Hes5$^{+ve}$ and GFAP$^{+ve}$. 40% expressed nestin, another marker for the precursor population. Accordingly in an embodiment the precursor cells are Hes5$^{+ve}$ and nestin$^{+ve}$. No co-labelling was observed with doublecortin, indicating that Hes5 does not label neuronal progenitors or newly born neurons. Thus the precursor cells are DCX$^{-ve}$. Accordingly, in an embodiment the cells selected for are Hes5$^{+ve}$, GFAP$^{+ve}$, nestin$^{+ve}$ and DCX$^{-ve}$. These studies were carried out using flow cytometry to sort the cells of GFP-Hes5, GFP-nestin and GFP-DCX animals.

It will be appreciated that any β3 adrenergic receptor agonist will be effective in activating the latent precursor cell population in view of the specific finding that norepinephrine acts through that receptor. Suitable β3 adrenergic receptor agonists are known to the person skilled in the art. They include norepinephrine and analogues, thereof, the selective β3-adrenoceptor agonist disodium 5-[(2R)-2-[[(2R)-2-(3-chlorophenyl)-2-hydroxyethyl]-amino]propyl]-1,3-benzodioxole-2,2-dicarboxylate, nebivolol, isoproterenol, SR58611, LY-368,842, Ro 40-2148, GW 427 353, L-796, 568, CL-316,245, BRL37344, CGP12177, members of the NRI family of anti-depressants such as reboxetine, atomoxetine and maprotiline. Various patents describe compounds said to have β3 adrenergic receptor agonist activity in relation to treatment of obesity and/or type II diabetes. For example, thiazole and oxazole-based compounds such as those disclosed in U.S. Pat. Nos. 5,786,356, 5,808,080 and 7,041,684, the contents of which are incorporated herein by reference, are suitable candidate compounds.

It has been observed that the cells most likely demonstrate the properties of self-renewal and multipotency are derived from neurospheres which are large in diameter, particularly those neurospheres larger in diameter than 110 μm and more particularly those neurospheres larger in diameter than 250 μm. Accordingly, in an embodiment neurospheres which have been subjected to activation and grow larger in diameter than 110 μm and more preferably larger in diameter than 250 μm are selected and prima facie identified as yielding a cell population in accordance with the invention for subsequent verification.

Differentiation and Proliferation.

The method of the invention may further comprise inducing differentiation and proliferation. The expanded and activated precursor cell population, or the progeny thereof following differentiation and proliferation, is likely to be useful in the treatment of neurodegenerative diseases to reverse the decline in the number of neurons characteristic of those diseases.

The precursor cell population of the present invention can been treated with one or more growth factors to induce differentiation, for example, into neurons and/or glia. In vitro proliferation and differentiation of neural stem cells is described, for example, in U.S. Pat. No. 7,115,418, the contents of which are incorporated herein by reference. The growth factors necessary to induce proliferation and/or differentiation are well known to the person skilled in the art and include, but are not, limited to, NGF, BDNF, the neurotrophins, CNTF, amphiregulin, FGF-1, FGF-2, EGF, TGFα, TGFβ, PDGF, IGFs and the interleukins.

Upon removal of the proliferation-inducing factor, proliferation of multipotent neural stem cells ceases. The neurospheres can be differentiated using the methods described above, for example by adhering the neurospheres to a substrate such as poly-ornithine-treated plastic or glass, where the precursor cells begin to differentiate into neurons and glial cells. Thus, the proliferation-inducing growth factor acts as an extrinsic signalling molecule that can be added or removed at will to control the extent of proliferation.

When the proliferation-inducing factor is removed, the factor responsive stem cell progeny can be co-cultured on a feeder layer. Many types of feeder layers may be used, such as fibroblasts, neurons, astrocytes, oligodendrocytes, tumour cell lines, genetically altered cell lines or any cells or substrate with bioactive properties. The feeder layer generally produces a broader range of phenotypes. In this instance, the feeder layer acts as a substrate and source of both membrane-bound and soluble factors that induce and alter the differentiation of the stem cell-generated progeny. Compared to a more inert substance, such as poly-L-ornithine, an astrocyte feeder layer, for example, induces a broader range of neuronal phenotypes as determined by indirect immunocytochemistry after 7 days in vitro. When differentiated on a poly-L-ornithine coated substrate with 1% FBS, neuronal phenotypes are almost exclusively GABAergic or substance P-ergic. When differentiated on an astrocyte feeder layer, in addition to GABAergic and substance P-ergic neurons, somatostatin, neuropeptide Y (NPY), glutamate and met-enkephalin-containing neurons are present. The astrocytes can be derived from tissue obtained from various brain regions such as the striatum, cortex and spinal cord.

Once the factor is removed, the culture medium may contain serum such as 0.5-1.0% FBS. Serum tends to support the differentiation process and enhance cell survival, especially when the differentiating cells are grown at a low density. However, it is possible to culture and differentiate the cells using defined conditions.

Within 1-3 days after removal of the factor and placing of the cell in conditions that support differentiation and survival, most or all of the precursor cells begin to lose immunoreactivity for nestin and begin to express antigens specific for neurons, astrocytes or oligodendrocytes. The identification of neurons is confirmed using immunoreactivity for the neuron-specific markers previously mentioned.

Screening Against Cell Population

Identification of a the neural cell population in which a latent precursor cell population which may be activated by treatment with a β3 adrenergic receptor agonist allows for methods for screening drug candidates for effectiveness in increasing neurogenesis.

In particular, the discovery of this latent precursor cell population opens the possibility that the in vivo population can be stimulated to proliferate and differentiate.

The precursor cell population of the present invention is also useful as a model for the screening of potential neurologically active therapeutic compounds.

Accordingly, in one aspect of the present invention there is provided a method of screening a potentially neurologically active therapeutic compound comprising the steps of:

(1) providing a neural cell population in which a latent neural precursor cell population capable of activation by treatment with a β3 adrenergic receptor agonist is present;

(2) contacting said neural cell population with at least one candidate pharmaceutical agent; and (3) determining if said candidate agent activates the latent precursor cell population.

In an alternative embodiment the effect of the candidate agent on a population in which the latent precursor cell population has been activated is determined.

In an embodiment, termed a "slice-sphere" assay, the method comprises:

(a) maintaining a slice from the hippocampus of an animal in contact with culture medium (b) introducing a candidate compound to said medium (c) subjecting the treated slice to mechanical degradation; and (d) culturing cells from the degraded slice in neurosphere-forming culture.

In this embodiment the number of neurospheres produced after a period in culture in neurosphere-forming medium is a measure of the extent of activation of the latent neural precursor cells.

In an embodiment the candidate compounds examined in the slice-sphere assay are from one of two major classes of widely prescribed antidepressants. In so doing it has been demonstrated that norepinephrine-selective reuptake inhibitors (NRIs) but not serotonin-selective reuptake inhibitors (SSRIs) significantly enhance hippocampal neural precursor activity. However it will be appreciated that the method is applicable to screening any candidate pharmaceuticals from any class of compound, as will be well understood by the person skilled the art. Screening assays may be performed directly using a culture. Candidate agents may be initially screened for the ability to modulate neurogenesis through its effect on an in vitro culture. For example, in a method which involves contacting the candidate drug and the culture of the present invention, the effect on differentiation and proliferation of the precursor cell population may be observed, but equally the effect on survival, phenotype or function of these cells or their progeny could be observed. An in vivo drug screening or drug discovery process involving engrafting a non-human mammal with an enriched population of neural stem cells is described in U.S. Pat. No. 7,105,150, the contents of which are incorporated herein by reference. The engrafted non-human mammal is useful for drug screening and drug discovery using well known methodology. Methods for screening a candidate agent against a cell culture are described, for example, in U.S. Pat. No. 7,041,438 using methods well known in the art. Assessment of the activity of candidate agents generally involves combining a cell culture with a candidate compound, determining any resultant change, and then correlating the effect of the compound with the observed change.

The observed effect may be either inhibitory or stimulatory. The occurrence of a biological response can be monitored using standard techniques known to those skilled in the art.

In embodiments of the invention potential neurologically therapeutic compositions can be applied to cells in culture at varying dosages, and the response of the cells monitored for various time periods. Physical characteristics of the cells can be analysed by observing cell and neurite growth with microscopy. The induction of expression of new or increased levels of proteins such as enzymes, receptors and other cell surface molecules, or of neurotransmitters, amino acids, neuropeptides and biogenic amines can be analysed with any technique known in the art which can identify the alteration of the level of such molecules. These techniques include immunohistochemistry using antibodies against such molecules, or biochemical analysis. Such biochemical analysis includes protein assays, enzymatic assays, receptor binding assays, enzyme-linked immunosorbant assays (ELISA), electrophoretic analysis, analysis with high performance liquid chromatography (HPLC), Western blots, and radioimmune assays (RIA). Other commonly used methods will be apparent to those of skill in the art. For example one may use fluorescent high-throughput screening of small molecules that induce neurogenesis in culture. In one assay of this type small molecules with neurogenesis-inducing activity in cells in culture can be rapidly identified by measuring the fluorescence intensity of the treated cells using a fluorescent microplate reader. Equally an adenosine triphosphate-based cell proliferation assay could be used to identify small molecules that activate or inhibit progenitor cell proliferation as described by Liu (Liu, 2009). Nucleic acid analysis such as Northern blots can be used to examine the levels of mRNA coding for these molecules, or for enzymes which synthesize these molecules. For example, inhibition or stimulation of a biological response may be identified by the level of expression of certain genes in the cells. Such genes may include early response genes such as fos, myc or jun (Greenberg, M. and Ziff, E., 1984). Other genes, including those which encode cell surface markers can also be used as indicators of the effects neuropharmacological compounds on the cells.

Alternatively, cells treated with these pharmaceutical compositions can be transplanted into an animal, and their survival, ability to form neuronal connections, and biochemical and immunological characteristics examined as previously described.

The precursor cells described above can be used in methods of determining the effect of candidate pharmaceuticals on neural cells. To determine the effect of a candidate pharmaceutical on neural cells, a culture of precursor cells derived from multipotent stem cells can be obtained and proliferated in vitro in the presence of a proliferation-inducing growth factor. The ability of various candidate pharmaceuticals to increase, decrease or modify in some other way the number and nature of the stem cell progeny proliferated in the presence of EGF or other proliferative factor can be determined. For example, it is possible to screen for candidate pharmaceuticals that increase the proliferative ability of progenitor cells which would be useful for generating large numbers of cells for transplantation purposes. It is also possible to screen for candidate pharmaceuticals which inhibit precursor cell proliferation. In these studies precursor cells are plated in the presence of the biological factor(s) of interest and assayed for the degree of proliferation which occurs. The effects of a biological agent or combination of candidate pharmaceuticals on the differentiation and survival of progenitor cells and their progeny can be determined. It is possible to screen neural cells which have already been induced to differentiate prior to the screening. It is also possible to determine the effects of the candidate pharmaceuticals on the differentiation process by applying them to precursor cells prior to differentiation. Generally, the biological agent will be solubilised and added to the culture medium at varying concentrations to determine the effect of the agent at each dose. The culture medium may be replenished with the biological agent every couple of days in amounts so as to keep the concentration of the agent somewhat constant.

Changes in proliferation are observed by an increase or decrease in the number of neurospheres that form and/or an increase or decrease in the size of the neurospheres (which is a reflection of the rate of proliferation-determined by the numbers of precursor cells per neurosphere).

The effects of the candidate pharmaceuticals are identified on the basis of significant difference relative to control cultures with respect to criteria such as the ratios of expressed phenotypes (neurons: glial cells, or neurotransmitters or other markers), cell viability and alterations in gene expression.

Electrophysiological analysis can be used to determine the effects of candidate pharmaceuticals on neuronal characteristics such as resting membrane potential, evoked potentials, direction and ionic nature of current flow and the dynamics of ion channels. These measurements can be made using any technique known in the art, including extracellular single unit voltage recording, intracellular voltage recording, voltage clamping and patch clamping. Voltage sensitive dyes and ion sensitive electrodes may also be used.

Screening Against β3 Adrenergic Receptor

Since the effects of norepinephrine have been found to be mediated through β3 adrenergic receptors, which are exclusively expressed by this neurogenic precursor pool, a method of screening a potentially neurologically active therapeutic compound also forms a part of the invention. In general terms such a method comprises the steps of:

(1) providing a β3 adrenergic receptor;
(2) contacting said β3 adrenergic receptor with at least one candidate pharmaceutical agent; and
(3) determining if said candidate agent binds to said β3 adrenergic receptor Utilizing the methods and compositions of the present invention, screening assays for the testing of candidate substances such as agonists and antagonists of β3 adrenergic receptors can be derived. A candidate substance is a substance which potentially can interact with or modulate, by binding or other intramolecular interaction, a β3 adrenergic receptor polypeptide.

Recombinant receptor expression systems may be used, as is well understood by the person skilled in the art, to prepare the β3 adrenergic receptor polypeptide as an alternative to tissue-based systems. The adrenergic β3 receptor (β3-adrenoceptor) is a member of the adrenergic receptor group of G-protein-coupled receptors that also includes α1A, α1B, α1D, α2A, α2B, α2C, β1 and β2. The human β3 receptor gene has been localized to chromosome 8 (8p12-8p11.1). Sequence information is available for the receptor as follows:

| | Adrenergic $\beta_3$ Receptor Gene Data | | |
|---|---|---|---|
| Species | Gene Symbol | Gene Accession No. | Protein Accession No. |
| Human | ADRB3 | NM_000025 | P13945 |
| Mouse | Adrb3 | NM_013462 | P25962 |
| Rat | Adrb3 | NM_013108 | P26255 |

Recombinant receptor expression systems make it possible to produce large quantities of receptors for use in screening assays. More important, however, is the relative purity of the receptor polypeptides provided. A relatively pure polypeptide preparation for assaying a protein agonist and/or antagonist interaction makes it possible to use elutive methods without invoking competing, and unwanted, side-reactions.

Cloned expression systems are also useful where there is difficulty in obtaining tissue that satisfactorily expresses a particular receptor. Cost is another very real advantage, at least with regard to the microbial expression systems of the present invention. For antagonists in a primary screen, microorganism expression systems of the present invention are inexpensive in comparison to tissue-screening methods.

In a further embodiment screening assays employing crude receptor preparations may be used. Typically, animal tissue slices thought to be rich in the receptor of interest are the source of the receptor. The tissue may be homogenized and the crude homogenate used as a receptor source.

Screening assays of the present invention generally involve determining the ability of a candidate substance to bind to the receptor and to affect the activity of the receptor, such as the screening of candidate substances to identify those that inhibit or otherwise modify the receptor's function. Typically, this method includes preparing recombinant receptor polypeptide, an extract comprising the receptor or cells comprising the receptor, followed by testing the polypeptide or cells expressing the polypeptide with a candidate substance to determine the ability of the substance to affect its physiological function. In preferred embodiments, the invention relates to the screening of candidate substances to identify those that affect human β3 adrenergic receptors, and thus can be suitable for use in humans.

As is well known in the art, a screening assay provides a receptor under conditions suitable for the binding of an agent to the receptor. These conditions include but are not limited to pH, temperature, tonicity, the presence of relevant co-factors, and relevant modifications to the polypeptide such as glycosylation or prenylation. It is contemplated that the receptor can be expressed and utilized in a prokaryotic or eukaryotic cell. The host cell expressing the receptor can be used whole or the receptor can be processed, partially purified or fully isolated from the host cell. The receptor can be membrane bound, integrated the membrane of the host cell or free in the cytosol of the host cell. The host cell can also be fractionated into sub-cellular fractions where the receptor can be found. For example, cells expressing the receptor can be fractionated into the nuclei, or the cytosolic fractions and the endoplasmic reticulum, vesicles, or the membrane surfaces of the cell isolated.

It is well known in the art that proteins can be reconstituted in artificial membranes, vesicles or liposomes. The present invention contemplates that the receptor can be incorporated into artificial membranes, vesicles or liposomes. The reconstituted receptor can be utilized in screening assays.

It is further contemplated that the receptor of the present invention can be coupled to a solid support. The solid support can be agarose beads, polyacrylamide beads, polyacrylic beads or other solid matrices including ELISA and culture plates capable of being coupled to proteins. Well known coupling agents include cyanogen bromide, carbonyldiimidazole, tosyl chloride, and glutaraldehyde.

In a typical screening assay for identifying candidate substances, one employs the same recombinant expression host as the starting source for obtaining the receptor polypeptide, generally prepared in the form of a crude homogenate. Recombinant cells expressing the receptor are washed and homogenized to prepare a crude polypeptide homogenate in a desirable buffer such as disclosed herein. In a typical assay, an amount of polypeptide from the cell homogenate is placed into a small volume of an appropriate assay buffer at an appropriate pH. Candidate substances, such as agonists and antagonists, are added to the admixture in convenient concentrations and the interaction between the candidate substance and the receptor polypeptide is monitored.

Where one uses an appropriate known substrate for the receptor, one can, in the foregoing manner, obtain a baseline activity for the recombinantly produced receptor. Then, to test for inhibitors or modifiers of the receptor function, one can incorporate into the admixture a candidate substance whose effect on the receptor is unknown. By comparing reactions which are carried out in the presence or absence of the candidate substance, one can then obtain information regarding the effect of the candidate substance on the normal function of the receptor.

Accordingly, it is proposed that this aspect of the present invention provides those of skill in the art with methodology that allows for the identification of candidate substances having the ability to modify the action of β3 adrenergic receptor polypeptides in one or more manners. In one embodiment, such an assay is designed to be capable of discriminating those candidate substances with desirable therapeutic properties but which lack undesirable properties. Also possible are studies that identify the molecular properties underlying the ability of agents to bind to and activate the receptors.

Additionally, screening assays for the testing of candidate substances are designed to allow the investigation of structure activity relationships of ligands with the receptors, e.g., study of binding of naturally occurring hormones or other substances capable of interacting or otherwise modulating with the receptor versus studies of the activity caused by the binding of such molecules to the receptor. In certain embodiments, the polypeptides of the invention are crystallized in order to carry out X-ray, crystallographic studies as a means of evaluating interactions with candidate substances or other molecules with the β3 adrenergic receptor polypeptide.

A screening assay of the invention, in preferred embodiments, conveniently employs a receptor polypeptide directly from the recombinant host in which it is produced. This is achieved, most preferably by simply expressing the selected polypeptide within the recombinant host, typically a eukaryotic host, followed by preparing a crude homogenate which includes the enzyme's activity. A portion of the crude homogenate is then admixed with an appropriate effector of the β3 adrenergic receptor, such as norepinephrine, along with the candidate substance to be tested. By comparing the binding of the selected effector to the receptor in the presence or absence of the candidate substance, one can obtain information regarding the physiological properties of the candidate substance.

A cell expressing a receptor can be used whole to screen agents. For example, cells expressing the receptor of the present invention can be exposed to radiolabeled agent and the amount of binding of the radiolabeled agent to the cell can be determined.

The cell expressing the receptor can be fractionated into sub-cellular components which contain the receptor of the present invention. Methods for purifying sub-cellular fractions are well known in the art. Sub-cellular fractions include but are not limited to the cytoplasm, cellular membrane, other membranous fractions such as the endoplasmic reticulum, Golgi bodies, vesicles and the nucleus. Receptors isolated as sub-cellular fractions can be associated with cellular membranes. For example, if cellular membrane vesicles are isolated from the cell expressing the receptor, the receptor molecule can be membrane bound. It is further contemplated that the receptor can be purified from a cell that expresses the receptor. Methods of purification are well known in the art. The purified receptor can be used in screening assays.

In that most such screening assays in accordance with the invention are designed to identify agents useful in initiating and/or stimulating neurogenesis.

There are believed to be a wide variety of embodiments which can be employed to determine the effect of the candidate substance on the receptor polypeptides of the invention, and the invention is not intended to be limited to any one such method. However, it is generally desirable to employ a system wherein one can measure the ability of the receptor polypeptide to bind to and or be modified by the effector employed in the presence of a particular substance.

The detection of an interaction between an agent and a receptor can be accomplished through techniques well known in the art. These techniques include but are not limited to centrifugation, chromatography, electrophoresis and spectroscopy. The use of isotopically labelled reagents in conjunction with these techniques or alone is also contemplated. For example, if an agent can bind to the receptor of the present invention, the binding can be detected by using radiolabeled agent or radiolabeled receptor. Briefly, if radiolabeled agent or radiolabeled receptor is utilized, the agent-receptor complex can be detected by liquid scintillation or by exposure to X-Ray film.

When an agent modifies the receptor, the modified receptor can be detected by differences in mobility between the modified receptor and the unmodified receptor through the use of chromatography, electrophoresis or centrifugation. When the technique utilized is centrifugation, the difference in mobility is known as the sedimentation coefficient. The modification can also be detected by differences between the spectroscopic properties of the modified and unmodified receptor. As a specific example, if an agent covalently modifies a receptor, the difference in retention times between modified and unmodified receptor on a high pressure liquid chromatography (HPLC) column can easily be detected.

As a specific example, if an agent, covalently modifies a receptor, the spectroscopic differences between modified and unmodified receptor in the nuclear magnetic resonance (NMR) spectra can be detected. Alternatively, one can focus on the agent and detect the differences in the spectroscopic properties or the difference in mobility between the free agent and the agent after modification of the receptor.

The interaction of an agent and a receptor can be detected by providing a reporter gene. Well known reporter genes include β-galactosidase (β-Gal), chloramphenicol transferase (CAT) and luciferase. The reporter gene is expressed by the host and the enzymatic reaction of the reporter gene product can be detected.

In preferred assays, an admixture containing the polypeptide, effector and candidate substance is allowed to incubate for a selected, amount of time, and the resultant incubated mixture subjected to a separation means to separate the unbound effector remaining in the admixture from any effector/receptor complex so produced. Then, one simply measures the amount of each (e.g., versus a control to which no candidate substance has been added). This measurement can be made at various time points where velocity data is desired. From this, one can determine the ability of the candidate substance to alter or modify the function of the receptor.

Numerous techniques are known for separating the effector from effector/receptor complex, and all such methods are intended to fall within the scope of the invention, for example, the use of thin layer chromatographic methods (TLC), HPLC, spectrophotometric, gas chromatographic/mass spectrophotometric or NMR analyses. It is contemplated that any such technique can be employed so long as it is capable of differentiating between the effector and complex, and can be used to determine enzymatic function such as by identifying or quantifying the substrate and product.

Development of highly selective, clinically useful β3 adrenergic receptor binding protein agonists will be facilitated by understanding the specific sites within the receptor necessary for agonist binding. There are three phases of the elucidation of agonists and antagonists: (1) binding assays to determine whether a candidate binds the peptide, (2) competitive binding studies to determine binding affinity and location, (3) receptor-ligand interaction studies.

EXAMPLES

Example 1

Adult Hippocampal Neurosphere Culture

Animals were treated in accordance with the Australian Code of Practice for the Care and Use of Animals for Scientific Purposes and ethics approval was obtained for all experiments from the Animal Ethics Committee of the University of Queensland. 8-10 week old male C57/B16 mice were killed by cervical dislocation and their brains removed. Brains were bisected along the midline in the sagittal plane. The hippocampi were isolated from the overlying cortex and minced using a scalpel blade. Minced tissue was digested in 0.1% papain (Invitrogen, Melbourne, Australia) for 20 minutes at 37° C., after which an excess of NeuroCult NSC basal medium (Stem Cell Technologies, Vancouver, Canada) was added to halt the digestion. Tissue was then centrifuged at 100 rcf for 5 minutes, the resulting pellet was resuspended in 1 ml of complete neurosphere medium, and a single cell suspension was achieved by gentle trituration. The cells were filtered through a 40 μm cell sieve (BD Biosciences, Sydney, Australia) and resuspended in NeuroCult NSC basal medium containing NeuroCult proliferation supplements (Stem Cell Technologies), 2% bovine serum albumin (Invitrogen) and 2 μg/ml heparin (Sigma-Aldrich, Sydney, Australia). The growth factors added were 20 ng/ml EGF (receptor grade, BD Biosciences) and 10 ng/ml bFGF (recombinant bovine, Roche, Basel, Switzerland). The cells were then plated in a 96-well plate and cultured in complete neurosphere medium containing EGF and bFGF, in the presence or absence of 5-hydroxytryptamine hydrochloride (serotonin; 100 nM, 1 μM, 10 μM), L-(−)-noradrenaline (+)-bitartrate salt monohydrate (norepinephrine; 100 nM, 1 μM, 10 μM) or KCl (15 mM). The adrenergic receptor antagonists used were prazosin (100 nM), yohimbine (1 μM), propranolol (1 μM), CGP20712 (10 nM), ICI118,551 (10 nM) and SR59230A (10 nM). BRL37344 was used as a selective β3 adrenergic receptor agonist. All the compounds were purchased from Sigma-Aldrich. The number of primary neurospheres was counted on day 10-13 and expressed as a percentage relative to the control.

It was found that norepinephrine but not serotonin activates adult hippocampal stem and precursor cells and promotes neurogenesis in vitro. The addition of serotonin at 100 nM, 1 μM or 10 μM produced no change in neurosphere numbers compared to the control. However, a significant increase was obtained in the presence of 100 nM and 1 μM norepinephrine, with an approximately 2-fold increase in neurosphere numbers observed in the presence of 10 μM norepinephrine (FIG. 1a). The neurospheres derived in the presence of 10 μM norepinephrine were also significantly, larger than the control neurospheres (FIG. 1b-d), with the emergence of a population of very large neurospheres greater than 200 μm in diameter (FIG. 1b, c). These resembled those described previously 5 following treatment with depolarizing levels of KCl, suggesting activation of a latent stem cell pool.

To determine whether the neurospheres generated demonstrated the characteristic stem-cell properties of self-renewal and multipotentiality the method employed in International Patent Application No. PCT/AU2008/000511 (WO2008/124872), the contents of which are incorporated herein by reference, was employed.

Hippocampal Neurosphere Passaging

To ascertain whether the norepinephrine-stimulated large neurospheres indeed reflected the activation of stem cells, individual neurospheres were selected and subjected to long-term passaging to assess their self-renewal capacity.

As a first step primary, neurospheres were individually dissociated and replated into fresh media not containing norepinephrine. Primary neurospheres from the unstimulated hippocampus were also passaged as single spheres. Hippocampal neurosphere cultures were initiated by removing 150 μl of the medium from wells containing single neurospheres, treating with 100 μl 0.1% trypsin-EDTA for 2 minutes at room temperature, followed by washing with 100 µl trypsin inhibitor in HEM. The neurospheres were mechanically triturated until dissociated and replated in 24 well plates in 2 ml of complete medium. Neurospheres were passaged every 10 days by centrifuging the neurospheres, removing the medium and incubating in 1 ml of 0.1% trypsin-EDTA for 2 minutes at room temperature. After the addition of an equal volume of trypsin inhibitor, the neurospheres were centrifuged at 100 rcf for 5 minutes and the supernatant removed. Cells were mechanically triturated in 500 µl of complete medium and trypan blue staining was used to evaluate the number of cells, both viable and total number, on a haemocytometer. The passaged cells were then re-plated with complete medium at a density of 1×104 cells/cm2 in tissue culture flasks (Nunc, Rochester, N.Y.) or tissue culture plates (Falcon/BD Biosciences) as appropriate.

A significant proportion (71.4%, 15 out of 21) of norepinephrine (10 µM) stimulated large neurospheres (>200 µm in diameter) could be passaged over 10 times (FIG. 2a) compared to none of the small neurospheres (<200 µm in diameter) from the control or norepinephrine-treated groups.

Immunocytochemistry

Figure 2:
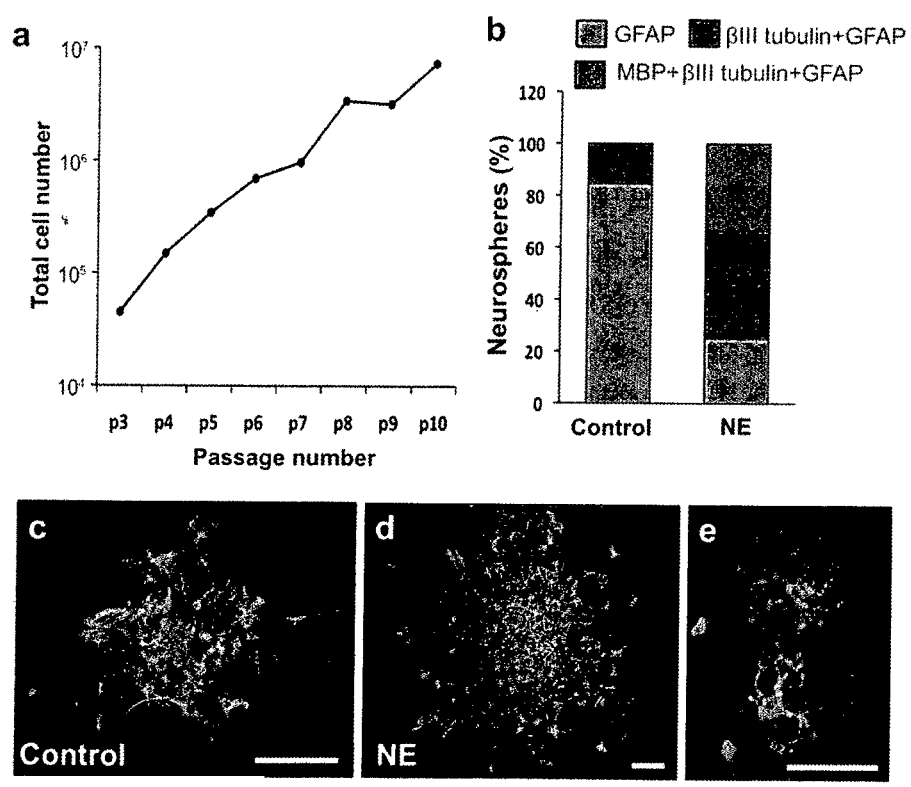
FIG. 2. Hippocampal precursors activated by norepinephrine are self-renewing and multipotent. (a) A large increase in cell numbers was observed when a single norepinephrine-derived large neurosphere was passaged up to ten times. (b) Relative percentage of the primary neurospheres expressing markers of astrocytes, neurons and oligodendrocytes in control vs norepinephrine (NE)-treated cultures. Note that all neurospheres examined contained GFAP-positive astrocytes. However, a significantly larger proportion of neurospheres expressed the neuronal marker βIII tubulin, in the norepinephrine-treated vs the control group. MBP-positive oligodendrocytes were only present in norepinephrine-stimulated neurospheres. An example of control (c) and norepinephrine-derived (d) neurospheres showing immunofluorescence for GFAP (green) and βIII tubulin (red). Nuclei were stained with DAPI (blue). Scale bars represent 100 μm. Note the presence of a large number of βIII tubulin-positive neurons in the norepinephrine-derived sphere. (e) MBP-expressing oligodendrocytes (green) were also present in norepinephrine-stimulated neurospheres. Scale bar, 30 μm.

We next determined the multipotentiality of the cells present within the neurospheres generated in the presence and absence of norepinephrine (FIG. 2b, c, d).

Control or norepinephrine-stimulated neurospheres were plated onto poly-ornithine-coated cover slips or poly-D-lysine-coated BioCoat eight-well culture slides (BD Biosciences) in serum-free basal medium without any mitogens. The neurospheres were allowed to flatten and adhere for 4-6 days in a humidified, 5% CO2 incubator. They were then fixed with 4% paraformaldehyde in 0.1M phosphate buffered saline (PBS) at 4° C. for 40 min, and immunocytochemistry was performed as described previously 38 using antibodies to the neuronal marker βIII tubulin (1:2000; Promega, Madison, Wis.), the astrocytic marker GFAP (1:500; DakoCytomation, Carpinteria, Calif.) and the oligodendrocyte marker MBP (1:500; Millipore, Sydney, Australia). 4',6'-diamidino-2-phenylindole (DAPI; 1:5000; Sigma-Aldrich) was used as a nuclear stain. Slides were mounted using fluoromount (Dako-Cytomation) and viewed on a Zeiss-Axio Imager microscope. Images were captured using a digital camera linked to a computer using Zeiss software.

Figure 3:
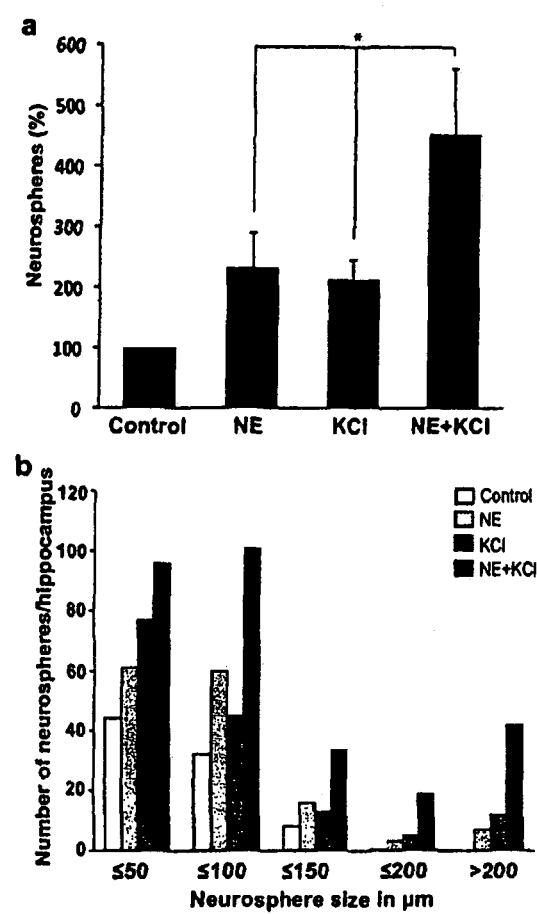
FIG. 3. Norepinephrine and KCl activate different populations of hippocampal precursors. (a) Culturing adult hippocampal cells in the presence of norepinephrine (NE) and KCl resulted in over a 4.5-fold increase in neurosphere numbers compared to a 2-fold increase in the number of neurospheres observed in the presence of either norepinephrine or KCl alone. (mean±SEM; n=2). (b) Distribution of neurospheres according to size showing more than a 3-fold increase in the number of large neurospheres, measuring >200 μm, obtained in the presence of NE+KCl.

All the neurospheres examined contained glial fibrillary acidic protein (GFAP)-expressing astrocytes. However, only a small proportion (4 out of 26 neurospheres examined) of the control neurospheres contained βIII tubulin-positive neurons as opposed to the majority (62 out of 82 neurospheres examined) of the norepinephrine-stimulated neurospheres. One third of the norepinephrine-stimulated neurospheres contained myelin basic protein (MBP)-positive oligodendrocytes (FIG. 2e), whereas none of the control neurospheres expressed the oligodendrocytic marker. Notably, all the norepinephrine-stimulated large neurospheres examined (n=9) contained >50 neurons. Together, these findings indicate, that norepinephrine but not serotonin can activate a self-renewing and multipotent precursor cell population in the adult hippocampus To examine whether norepinephrine and KCl activate the same latent pool of precursors, we added both KCl (15 mM) and norepinephrine (10 µM) to the cultures. This led to an approximately 4.5-fold increase in total neurosphere numbers compared to the 2-fold increase observed in the presence of either norepinephrine or KCl alone, suggesting that separate populations of precursors were being activated (FIG. 3a). More importantly, the increase in the number of large neurospheres (>200 µm in diameter) was approximately 3-fold (FIG. 3b).

Example 2

Hes5-GFP Model

Mice expressing GFP under the control of the Hes5 promoter were generated using standard techniques. Hes5-GFP mice were perfused transcardially using ice-cold 4% paraformaldehyde. Brains were removed and post-fixed in 4% paraformaldehyde for 24 hours, after which 50 µm sections were cut using a freezing microtome. The sections were blocked in PBS containing 0.1% Triton X-100 (0.1% PBTX) and 10% normal goat serum for 1 hour and then labelled with primary antibodies: anti-GFAP (1:500; DakoCytomation), anti-doublecortin (1:500; Sapphire Bioscience, Sydney, Australia) and anti-nestin (1:100, Developmental Studies Hybridoma Bank, Iowa City Iowa). The sections were washed three times using 0.1% PBTX and incubated for 2 hours at room temperature with the secondary antibodies goat anti-mouse Alexa 568 or goat anti-rabbit Alexa 568 (Invitrogen), and DAPI (1:1000). BrdU immunohistochemistry was performed essentially as described previously (Kulkarni et al., 2002, Jha et al., 2006). In brief, this involved DNA denaturation and acid hydrolysis followed by overnight incubation with mouse anti-BrdU antibody (1:500; Roche, Sydney, Australia). The secondary antibody goat anti-mouse Alexa 488 (Invitrogen) was used at 1:2000. After several washes, the sections were mounted using fluoromount (DakoCytomation) and viewed on a Zeiss-Axio Imager microscope. Optical sectioning was achieved using ApoTome and images were captured using a digital camera linked to a computer using Zeiss software.

For double label immunofluorescence for GFP and GFAP in nestin-GFP mice, 4 sections (50 µm) were selected per animal. The choice of sections was such that they were from comparable Bregma points across all experimental animals. The sections were incubated for 2 hours with 10% horse serum (Invitrogen) before an overnight incubation at room temperature with a mixture of the primary antibodies, rabbit anti-GFP (1:500, Invitrogen) and mouse anti-GFAP (1:1000, Sigma). Sections were then incubated with the secondary antibodies, donkey anti-rabbit IgG (1:250, Invitrogen) and donkey anti-mouse IgG (1:250, Invitrogen) for 4 hours at room temperature.

Cell counting analysis was performed on coded sections by an experimenter blind to the study code. To address the effects of β adrenergic receptor stimulation on nestin/GFAP double-positive quiescent progenitors, the percentage of GFP-positive cells that co-localized with GFAP was determined by confocal microscopy using an Olympus FV1000 confocal microscope. 30-40 GFP-positive cells from four sections (250 µm apart) per animal were analyzed using z-plane confocal sectioning with 1 µm steps to confirm co-localization of GFP with GFAP.

Fluorescence-Activated Cell Sorting

Brains from 8-12 weeks old male Hes5-GFP mice were removed and hippocampi were isolated as described earlier. A live cell suspension was prepared from the hippocampus using 0.1% papain, and the dead cells were labelled with propidium iodide (1 µg/ml). GFP-positive and -negative cells were then purified by fluorescence-activated cell sorting (FACS). Cells were sorted on a FACS Vantage (Becton Dickinson, Melbourne, Australia) with DIVA software. The GFP-negative populations was set relative to the basal fluorescence levels obtained from GFP-negative wild-type littermate controls and a conservative approach was used in selecting only high GFP-expressing cells. The cells were collected in basal medium and plated into 96-well tissue culture plates in medium containing EGF+bFGF with or without norepinephrine (10 μM).

RNA Extraction and cDNA Synthesis

RNA was extracted from sorted Hes5-GFP-positive and -negative cells using the RNeasy Mini Kit (Qiagen, Venlo, Netherlands). Genomic DNA was removed by DNAse digestion using a DNA-free kit (Ambion, Austin, Tex.). cDNA was generated using SuperScript III (Invitrogen, Carlsbad, Calif.) with oligo-dT primers.

PCR

Figure 5:
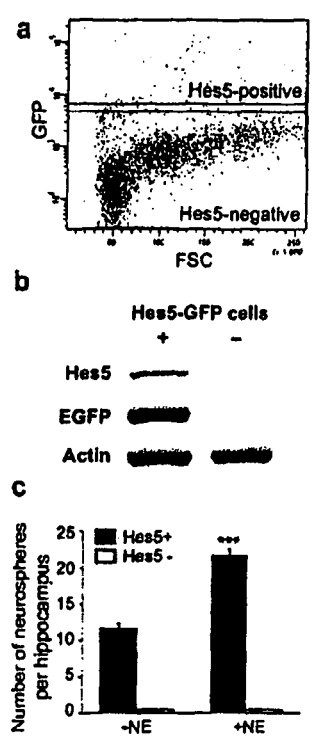
FIG. 5. Norepinephrine activates a Hes5-expressing precursor population. (a) Hes5-GFP-positive and -negative cells were sorted using flow cytometry based on their GFP expression. FSC; Forward scatter (b) Reverse transcriptase-PCR analysis revealed the presence of Hes5 mRNA only in the GFP-positive population. (c) The Hes5-GFP-positive population contained all the neurosphere-forming cells. Note that in presence of norepinephrine almost twice as many neurospheres were obtained from the Hes5-GFP-positive population. No neurospheres were generated from the Hes5-GFP-negative population.

The complete list of primer sequences used for the polymerase chain reaction is detailed in Table 1. The program 1 involved initial denaturation at 95° for 2 minutes, followed by 35 cycles of 95° for 1 minute and 70° for 2 minutes, with a final elongation step of 72° for 5 minutes as described by Cikos et al. (Cikos, 2005). Program 2 began with initial denaturation at 95° for 2 minutes, followed by 32 cycles of 95° for 30 seconds, 64° for 30 seconds and 72° for 30 seconds, essentially as described by Evans et al (Evans, 1999). 45 cycles were used to amplify the β3 receptor (Adrb3).

scriptase-PCR analysis of the sorted cells showed the presence of Hes5 mRNA only in the GFP-positive population (FIG. 5b), which represented 5.6±0.5% (n=5 experiments) of the total viable hippocampal population. Subsequently, GFP-positive and -negative cells purified using flow cytometry were cultured for neurosphere generation. Approximately 1 out of 65.5±15.2 GFP-positive cells gave rise to a neurosphere in control medium containing EGF and bFGF, with no neurospheres being obtained from the GFP-negative fraction (FIG. 5c). More importantly, the addition of norepinephrine resulted in a 2-fold increase in neurosphere numbers only in the GFP-positive population (FIG. 5c), with the appearance of very large neurospheres (>200 μm in diameter) as described above (control: 1.0±0.5 neurospheres vs NE: 7.3±0.8 neurospheres per hippocampus). Together, these findings identify Hes5 as a marker of the norepinephrine-responsive stem and progenitor cell population in the adult hippocampus.

Finally, to determine whether norepinephrine activated the precursor cell population directly and not via release of other factors in a paracrine fashion in the bulk cultures, Hes5-GFP-positive cells were plated at a clonal density in 96-well plates. Approximately 1 out, of 32.5±0.1 GFP-positive cells formed

TABLE 1

Gene specific primer sequences for reverse transcriptase-PCR

| Target | Forward | Reverse | Product | Program |
|---|---|---|---|---|
| Adrb1 | ggagctccctcggacgac | agcctggctctctacaccttg | 173 bp | 1 |
| Adrb2 | gtactgtgcctagccttagcgt | ggttagtgtcctgtcaaggagg | 115 bp | 1 |
| Adrb3 | tctagttcccagcggagttttcatcg | cgcgcaccttcatagccatcaaacc | 234 bp | 2* |
| Hes5 | aagtaccgtggcggtggagatgc | cgctggaagtggtaaagcagctt | 354 bp | 2 |
| EGFP | cctacggcgtgcagtgcttcagc | cggcgagctgcacgctgcgtcctc | 300 bp | 2 |
| Actin | agaagagctatgagctgcctgacg | tacttgcgctcaggaggagcaatg | 301 bp | 2 |

Norepinephrine Directly Stimulates Proliferation of a Hes5-Expressing Stem and Precursor Cell Population.

Figure 4:
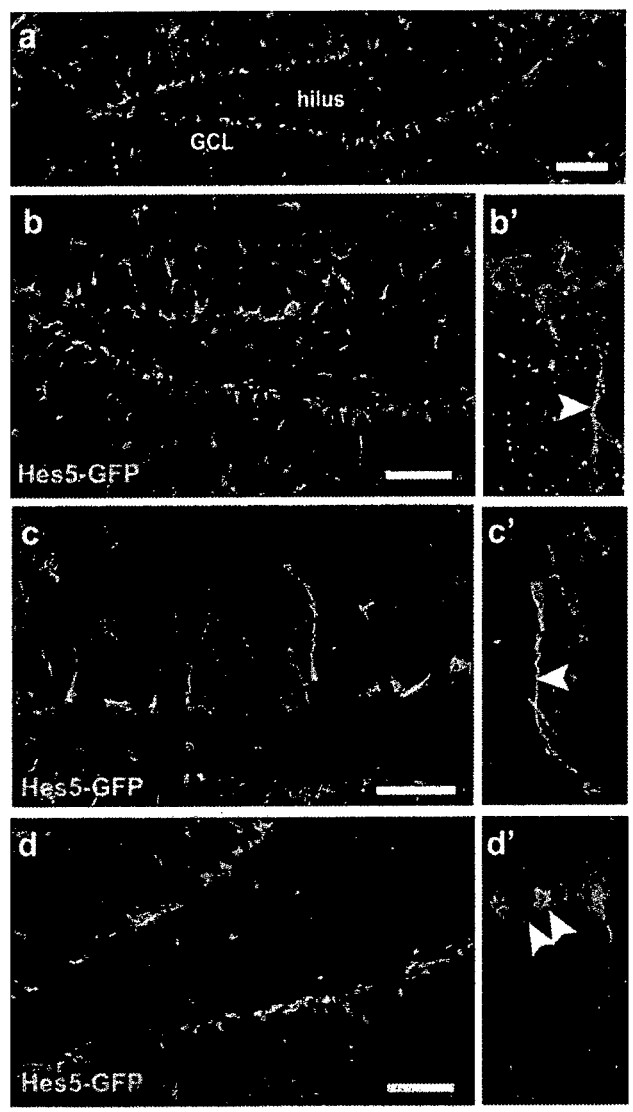
FIG. 4. Hes5-GFP-positive cells co-express markers of stem cells in the adult dentate gyrus. (a) Hes5-GFP-positive cells are predominantly present along the subgranular zone and extend radial-glia like processes through the granule cell layer (GCL) in the adult dentate gyrus. Hes5-GFP-positive cells co-express markers of stem cells such as GFAP (red; b) and nestin (red; c). The co-expression is seen predominantly along the processes of the Hes5-GFP-positive cells (arrowheads; b', c'). No co-expression was seen with doublecortin (red; d), a marker of newly born neurons. However, doublecortin-positive cells were mainly found in juxtaposition with Hes5-GFP-positive cells (arrowheads; d'). Nuclei were labelled with DAPI (blue). Scale bars, 100 μm.

We examined the expression pattern in the adult hippocampus and found that GFP-expressing cells were predominantly located along the subgranular zone (SGZ) of the dentate gyrus and that these cells had a radial glia-like morphology (FIG. 4a). The restricted expression and the characteristic morphology of the Hes5-GFP-positive cells prompted us to further examine whether this population represented stem/precursor cells. Upon co-labelling with known stem/precursor cell markers, we found that 39% of the Hes5-GFP-positive cells in the SGZ (total of 927 cells examined) expressed GFAP, a marker for quiescent neural precursor or neural stem-like cells (FIG. 4b, b') whereas 40% expressed nestin, another marker for the precursor population (total of 477 cells examined; FIG. 4c, c'), suggesting that Hes5-GFP-positive cells were part of a stem/precursor cell population. No co-labelling was observed between doublecortin- and GFP-positive cells (FIG. 4d), indicating that Hes5-GFP does not label neuronal progenitors, or newly born neurons, although several doublecortin-positive cells were found in juxtaposition with GFP-expressing cells in the SGZ (FIG. 4d').

Next, to examine the stem cell potential of the Hes5-GFP-expressing cells, cells were sorted from the adult hippocampus based on GFP expression (FIG. 5a). Reverse trana neurosphere in the control medium, with a 215.4±23.5% increase in neurosphere numbers being observed in the norepinephrine-treated wells, unequivocally demonstrating that norepinephrine can directly activate the precursor cell population. Moreover, a number of large neurospheres (>200 μm) expressing GFP were also observed in the presence of norepinephrine (data not shown).

Example 3

β3-Adrenergic Receptors Mediate the Effects of Norepinephrine

Figure 6:
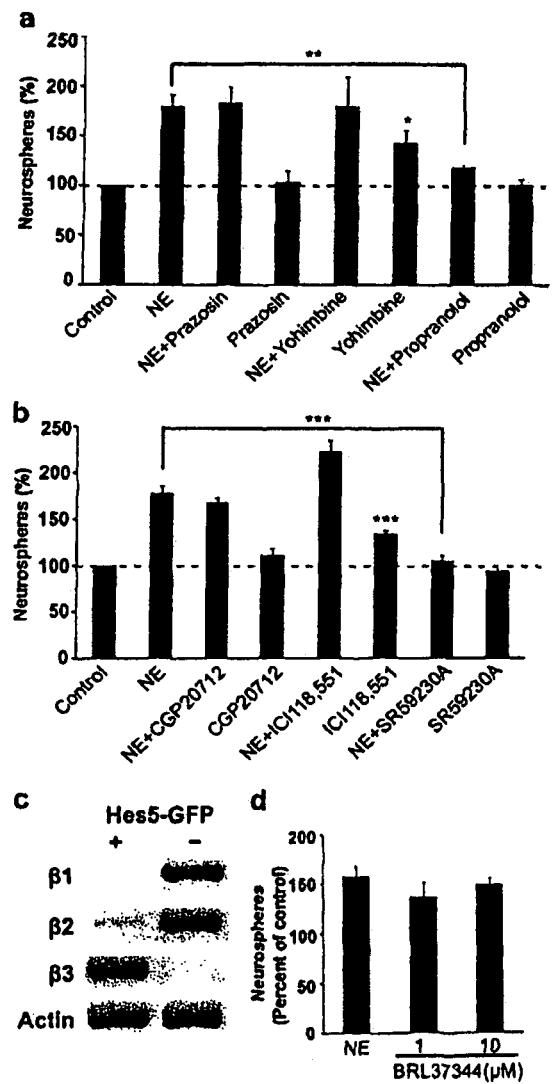
FIG. 6. β3 receptors are expressed on neural precursors, and mediate the norepinephrine-dependent activation. (a) Neither the α1 adrenergic receptor antagonist prazosin nor the α2 adrenergic receptor blocker yohimbine had any effect on the norepinephrine-stimulated increase in neurosphere numbers. Only the β-adrenergic receptor blocker, propranolol, completely inhibited the norepinephrine-stimulated increase in neurosphere numbers. Note that treatment with propranolol alone had no toxic effect on neurosphere production. A slight but significant increase in the number of neurospheres was also observed in the presence of yohimbine alone. (b) The selective β3 blocker SR59230A completely inhibited the norepinephrine-mediated increase in neurosphere numbers. In contrast, the β1 and β2 receptor antagonists, CGP20712 and ICI118,551, respectively, had no such effect. Note the significant increase in neurosphere numbers in the presence of ICI118,551 alone. (c) Expression of β adrenergic receptors in the sorted population of Hes5-GFP-positive and -negative cells by reverse transcriptase-PCR showed the presence of the β3 adrenergic receptor exclusively in the Hes5-positive population, whereas β1 and β2 adrenergic receptor transcripts were expressed predominantly in the Hes5-negative population. Note that a small amount of β2 receptor mRNA was also detected in the Hes5-positive population. (d) A similar increase in neurosphere numbers was observed in the presence of a selective β3 adrenergic receptor agonist BRL37344 at 1 μM and 10 μM, compared to treatment with norepinephrine. (*p<0.05; p<0.011 *p<0.001)

Given that norepinephrine directly activated hippocampal precursors, we next sought to identify the adrenergic receptor(s) mediating this effect. Adrenergic receptors are a diverse family of receptors divided into, two major subclasses, α and β, with six members of the α family and three members of the β family identified to date. The hippocampal cells were treated with specific antagonists to α1 adrenergic receptors (prazosin), α2 adrenergic receptors (yohimbine), or β adrenergic receptors (propranolol) in the presence or absence of norepinephrine (FIG. 6a). Both prazosin (100 nM) and yohimbine (1 μM) failed to inhibit the increase in neurosphere numbers observed in the presence of norepinephrine, whereas propranolol (1 μM) reduced the norepinephrine-mediated response back to control levels (F=0.004), suggesting that β adrenergic receptors are required for norepinephrine-dependent activation of precursors. Interestingly, treatment with yohimbine alone resulted in a significant 40% increase (p=0.012) in the neurosphere numbers compared to the control.

Next, to identify the subtype of β adrenergic receptor involved, we tested specific antagonists (FIG. 6b). CGP20712 (10 nM), a β1 adrenergic receptor antagonist, had no effect, whereas the β2 adrenergic receptor blocker ICI118,551 (10 nM) significantly enhanced (p=0.019) the norepinephrine-mediated response, Moreover, ICI118,551 in the absence of norepinephrine also increased neurosphere generation by about 34% (p=0.0005) compared to the control. Only. SR59230A (10 nM), a specific β3 adrenergic receptor antagonist, completely blocked the norepinephrine-mediated activation of precursors (p=0.0008), and also significantly reduced the generation of very large neurospheres (NE: 12±2.08 neurospheres vs NE+SR59230A: 3.33±0.88 neurospheres). A similar block in norepinephrine-mediated activation was observed when the purified Hes5-GFP-positive precursor population was treated with SR59230A (control: 28±1.0 neurospheres, NE: 45.5±2.5 neurospheres, NE+SR59230A: 26.5±2.5 neurospheres; n=2 experiments).

Figure 10:
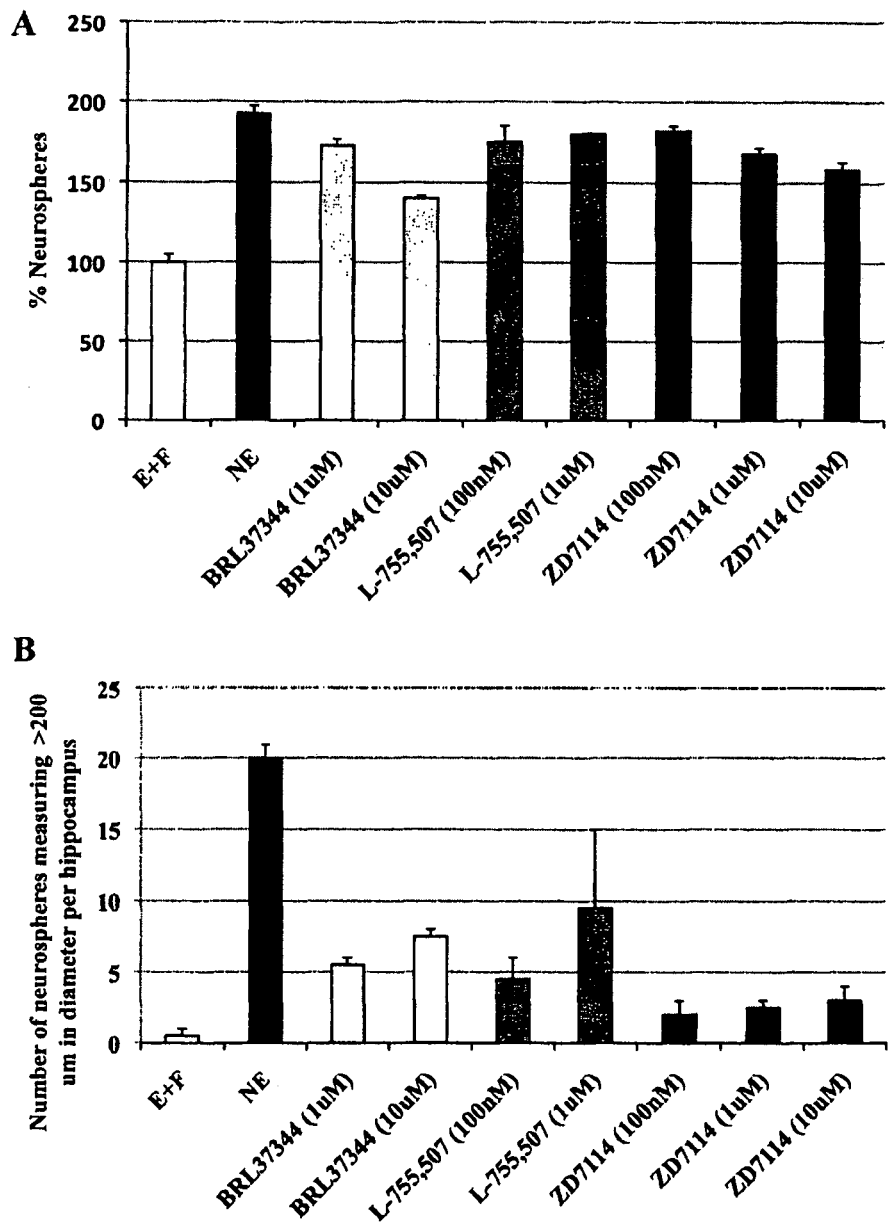
FIG. 10. Effects of several selective β3 adrenergic receptor agonists on hippocampal neural precursors in vitro. (A) A similar increase in the total number of neurospheres was observed when neural precursors were treated with several selective β3 adrenergic receptor agonists compared to those treated with 10 μM norepinephrine. (B) Treatment with β3 adrenergic receptor agonists activates stem-like cells resulting in generation of large neurospheres measuring more than 200 μM in diameter.

Importantly, reverse transcriptase-PCR analysis showed the presence of β3 adrenergic receptors exclusively in the Hes5-positive population, whereas α1 and β2 adrenergic receptors were expressed predominantly in the Hes5-negative population (FIG. 6c). A small amount of β2 adrenergic receptor was also detected in the Hes5-positive, cells. Consistent with the above findings, addition of a specific β3 adrenergic receptor agonist BRL37344, at both 1 μM and 10 μM, led to an increase in neurosphere numbers similar to that observed in the presence of 10 μM norepinephrine (FIG. 6d). A similar increase was observed with other selective β3 adrenergic receptor agonists (FIG. 10).

Example 4

Hippocampal Organotypic Slices

Generation of Hippocampal Organotypic Slices

Seven day-old Wistar pups were sacrificed under isoflurane-induced anaesthesia, and the brains were isolated and placed in ice-cold Ringer's solution (NaCl, 118 mM; KCl, 2.5 mM; $NaH_2PO_4$, 1.2 mM; $CaCl_2$, 2.5 mM; $MgCl_2$, 1.3 mM, $NaHCO_2$, 25 mM and glucose, 10 mM; pH 7.2). The brain was bisected along the sagittal plane and the hippocampi were separated from the overlying cortex. The hippocampi were cut into transverse slices of 300 μm thickness using a tissue slicer (Stoelting, Wood Dale, Ill.). 6-7 slices were then transferred onto a single 0.4 μm Millicell-CM membrane filter (Millipore), and the filters were placed in a 6-well plate containing 1 ml of serum-free NeuroCult NSC basal medium with NeuroCult proliferation supplements (StemCell Technologies) and 2% bovine serum albumin (Invitrogen). D-glucose (Sigma-Aldrich) was added to the medium to a final concentration of 5 mM. Four filters, each containing 6-7 hippocampal slices, were generated from a single animal. Plates were incubated at 37° C. in a humidified 5% $CO_2$ incubator and the slices were cultured for 6 days.

Pharmacological Treatment of Hippocampal Slices

To assess the influence of specific compounds on hippocampal precursor proliferation in the slice culture, compounds were added to the complete medium at the doses described below. Two filters were treated with the compounds for each dose per experiment. On every alternate day half the medium was removed and replaced with fresh medium containing the compounds. Slices were treated with serotonin at 10 μM and 100 μM and norepinephrine at 1 μM, 10 μM and 100 μM. The antidepressants used were fluoxetine (1 μM and 10 μM), citalopram (10 μM and 100 μM), reboxetine (1 μM, 10 μM and 100 μM), atomoxetine (1 μM) and maprotiline (1 μM). Propranolol (10 μM) was used to block β adrenergic receptors in the slices.

Derivation of Neurospheres from Hippocampal Organotypic Slices

On the $6^{th}$ day of culture, the hippocampal slices from each treatment group were pooled and the tissue was minced using a scalpel blade. Minced tissue was then treated with 0.1% trypsin-EDTA (Invitrogen) for 5 minutes at 37° C. The digestion was stopped by adding 0.014% w/v trypsin inhibitor (Sigma-Aldrich Australia). A single cell suspension was achieved by gentle trituration. The total number of viable cells in an aliquot was counted on a haemocytometer based on the exclusion of 0.08% trypan blue (Sigma-Aldrich). The cells were then cultured in complete neurosphere medium containing EGF and bFGF. A 200 μl cell suspension was plated at 2500 cells/ml in a 96-well plate, resulting in a cell density of 500 cells/well. For each experiment there were 20 wells plated for each of the doses per treatment group. The plates were incubated at 37° C. in a humidified 5% $CO_2$ incubator. The number of neurospheres obtained per well was counted after 10 days in culture and expressed as a percentage of the control.

Norepinephrine but not Serotonin Increases Hippocampal Precursor Activity in a Novel 'Slice-Sphere' Assay Ex Vivo The above finding that norepinephrine but not serotonin directly activates hippocampal precursors prompted us to examine whether agents such as antidepressants, which act primarily by modulating levels of these neurotransmitters, exert their neurogenic effects by directly regulating hippocampal precursor activity. Given that the primary target of actions for these drugs requires the presence of monoaminergic terminals, which can be maintained only in an intact neurogenic niche, we reasoned that the neurosphere assay, where such a niche would be lost, was less suitable for this purpose. The two-step slice-sphere assay (outlined in FIG. 7a-d), combines the advantages of organotypic slices, which retain the neurogenic milieu, and the neurosphere assay, which serves as a measure of quantifying precursor numbers. Hippocampal organotypic slices prepared from 7-day-old neonatal rats retained a healthy appearance after 6 days ex vivo in a serum-free culture medium. Although a significant reduction of about 34% in cell number (n=4 experiments, p=0.003) was observed from the slices cultured for 6 days ($1.43 \times 10^5 \pm 1.57 \times 10^4$ cells/ml) compared to acute slices (day 0: $2.17 \times 10^5 \pm 1.12 \times 10^4$ cells/ml), the frequency of neurosphere formation was remarkably similar at day 0 (28.46±0.6 neurospheres per 500 cells) and day 6 (25.01±2.1 neurospheres per 500 cells; p=0.216), indicating not only that the precursors were maintained in the slices but also that they retained their normal proliferative capacity.

Figure 7:
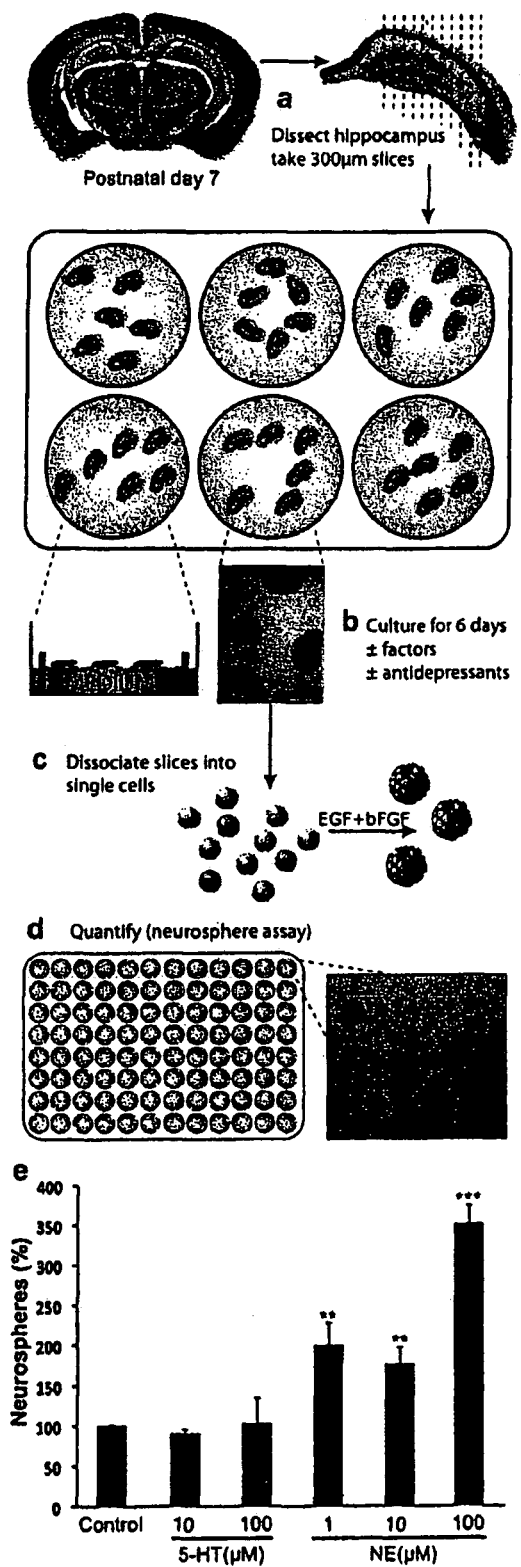
FIG. 7. Direct application of norepinephrine but not serotonin enhances hippocampal precursor activity in the slice-sphere assay. (a) The hippocampus from a postnatal day 7 Wistar rat was dissected and cut transversely into 300 μm slices. The slices were placed on a 0.4 μm membrane filter that was bathed in 1 ml of complete serum-free NeuroCult medium in a 6-well plate. 4 filters, each containing 6-7 slices, were generated from a single animal. (b) The organotypic slices were cultured at a liquid-air interphase for a period of 6 days. Antidepressants or compounds were added to the medium on day 1 and half the medium was replaced with fresh medium every alternate day. (c) On the $6^{th}$ day, the hippocampal slices were enzymatically dissociated and cells were plated in a 96-well plate and cultured in the presence of EGF and bFGF to obtain neurospheres. (d) The number of neurospheres generated was quantified after 10-12 days in culture, this being representative of the number of proliferating hippocampal precursors present in the slices. (e) Serotonin (5-HT) treatment had no effect on the frequency of neurosphere formation either at 10 μm or 100 μM (p>0.05). However, direct application of norepinephrine (NE) to the slices resulted in an approximately 2-fold increase in the neurosphere frequency at 1 μM and 10 μM, and a 3.5 fold increase at 100 μM ( p<0.01; * p<0.001).

To determine the influence of an intact neurogenic niche in mediating the effects of serotonin or norepinephrine on precursor activity, hippocampal slices were treated with various concentrations of these neurotransmitters. The neurosphere frequency remained unchanged in the slices treated with serotonin (10 μM: 90.07±5.4% and 100 μM: 102.81±31.7%) compared with the control (FIG. 7e). However, a remarkably similar 2-fold increase in precursor numbers was obtained in the slice-sphere assay from slices treated with either 1 μM (p=0.026) or 10 μM norepinephrine (p=0.023), consistent with our finding of an enhanced neurosphere frequency in the conventional neurosphere assay. Notably, addition of 100 µM norepinephrine to the slices led to a 3.5 fold increase (p=0.000069) in the precursor activity compared to the control. This suggests that serotonin is not able to modulate precursor activity even when the neurogenic niche is maintained. Moreover, it highlights the importance of an intact neurogenic niche in revealing a significantly larger increase in norepinephrine-dependent precursor activation than observed in the standard neurosphere assay.

Example 5

Activity of Antidepressants in the Slice-Sphere Assay

Figure 8:
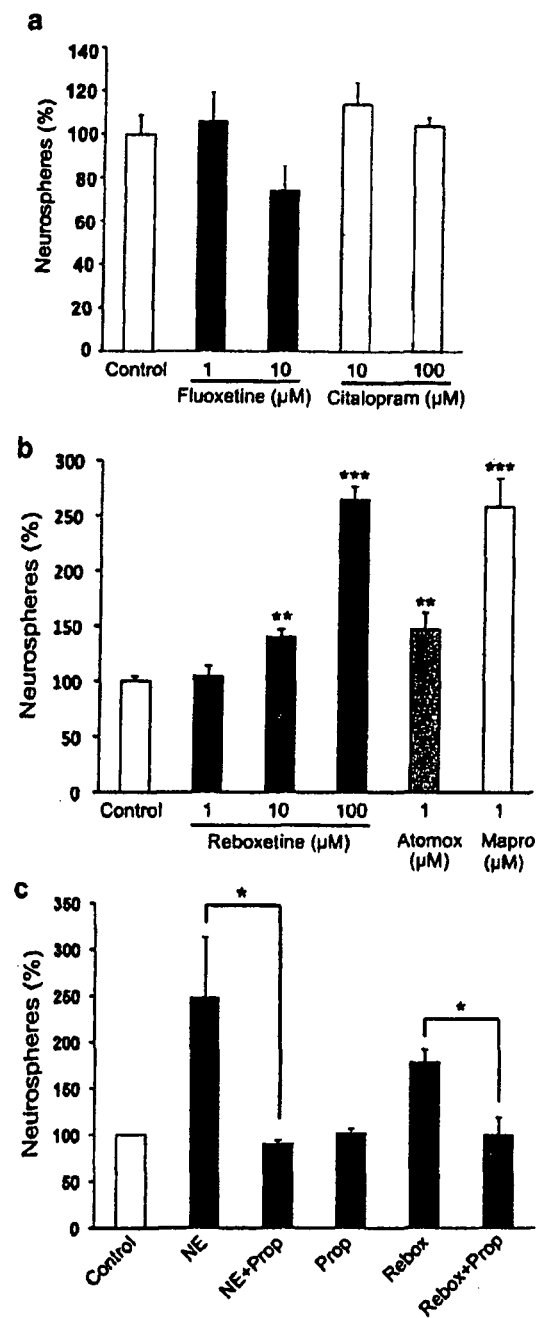
FIG. 8. NRIs but not SSRIs increase the activity of hippocampal precursors in the slice-sphere assay. (a) Slices treated with the SSRIs fluoxetine (1 μM and 10 μM) or citalopram (10 μM and 1000 μM) showed no significant change in the frequency of neurosphere generation compared to the untreated slices (control). (b) Reboxetine, a prototypical NRI, significantly enhanced the frequency of neurosphere formation at 10 μM and 100 μM. Treatment of slices with atomoxetine and maprotiline also resulted in a significant increase in neurosphere frequency. (c) Blockade of β adrenergic receptors by propranolol abolished both the norepinephrine- and the reboxetine-mediated increase in neurosphere frequency. (*p<0.05;  p<0.01; * p<0.001).

Finally, the above findings led us to examine the effect of two major classes of antidepressants on hippocampal precursor activity. Fluoxetine, a prototypical SSRI, had no effect on precursor numbers when added to the slices at a concentration of either 1 µM or 10 µM (FIG. 8a; p>0.05). Although fluoxetine is a potent uptake inhibitor of serotonin, it is also known to affect the activity of muscarinic, histaminergic and a adrenergic receptors[25]. Hence, the effect of another potent and more specific SSRI, citalopram, was also examined. Again, no significant change in the hippocampal precursor frequency was observed at either. 10 µM (113.8±9.9%) or 100 µM (103.8±3.8%) citalopram compared to the control (FIG. 8a).

In contrast, reboxetine, a widely used NRI, produced a dose-dependent increase in neurosphere numbers. While the frequency of neurosphere formation remained unchanged at 1 µM (104.5±9.6%), a significant 40% increase was observed at 10 µM (p=0.0026), and more than a 2.5 fold increase was observed at 100 µM (265.0±11.7%; p=0.00015); (FIG. 8b). This stimulatory effect on hippocampal precursors was not exclusive to reboxetine, being observed in the presence of other members of the NRI family, namely atomoxetine and maprotiline (FIG. 8b). Atomoxetine, at a concentration of 1 µM, increased the precursor frequency to 147.0±15.0% (n=2 experiments), comparable to that obtained with 10 µM reboxetine treatment. Treatment of slices with 1 µM maprotiline produced an even greater increase (258.5±25.5%) in the frequency of neurosphere formation compared to the control (n=2 experiments). Taken together, these results suggest that antidepressants that specifically block the reuptake of norepinephrine may exert their neurogenic effects in the hippocampus primarily through activation of a precursor population. In contrast, serotonin and the antidepressants that modulate its levels appear to have no direct role in regulating hippocampal precursor activity.

Finally, to determine whether the norepinephrine- and reboxetine-mediated increase in hippocampal precursor activity involves β adrenergic receptors, slices were treated with propranolol in the presence of either norepinephrine or reboxetine (FIG. 8d). The ability of propranolol to completely inhibit the norepinephrine-mediated (p=0.036) as well as the reboxetine-mediated (p=0.013) increase in precursor activity confirmed the involvement of β adrenergic receptors.

Example 6

Figure 9:
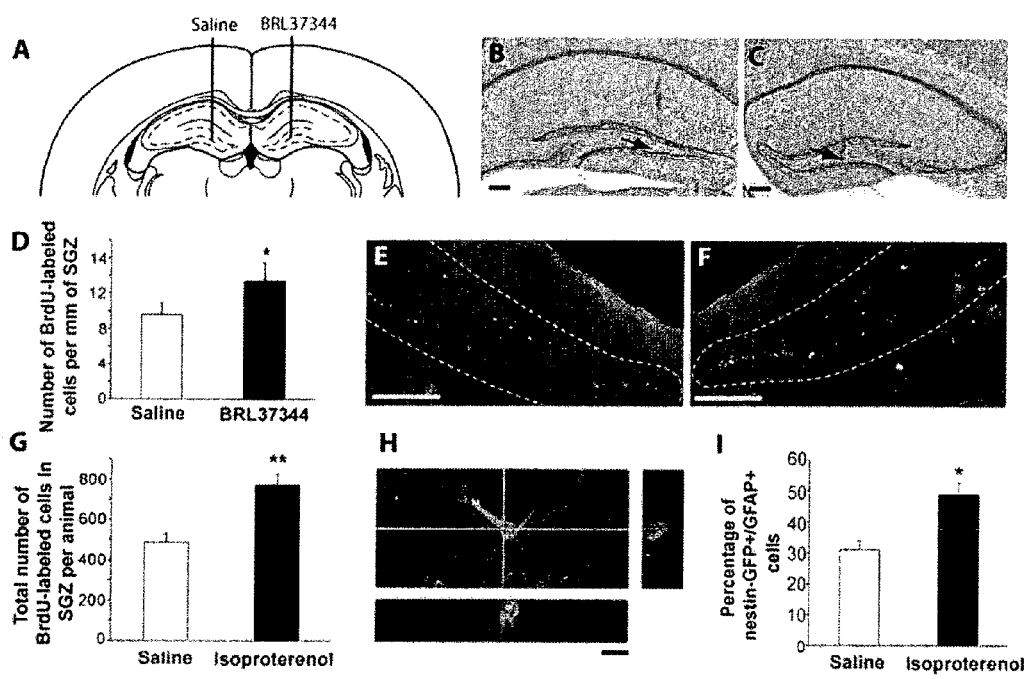
FIG. 9. Stimulation of β3 adrenergic receptors increases proliferation of hippocampal precursors in vivo. (A-C) Bilateral intrahippocampal microinfusion was verified on Nissl-stained sections. (A) A representative coronal section showing the injection track terminating in the hilus region of the hippocampus (Paxinos and Franklin, 2001). The hilus from one hemisphere received a 0.5 μl injection of 10 μM BRL37344 with the contralateral hemisphere receiving a control injection of 0.9% saline. (B, C) Nissl-stained sections showing the most ventral point of the microinfusion track (arrows) following infusion of 0.9% saline (B) or BRL37344 (C). Scale bars, 200 μm. (D) A significant increase was observed in the linear density of BrdU-positive cells in the SGZ of the BRL37344-injected hippocampus compared to the contralateral saline-injected hippocampus (*p<0.05). A representative micrograph showing BrdU-labeled cells along the SGZ in saline-treated (E) vs BRL37344-treated (F) hippocampus. The granule cell layer is delineated by the dashed lines. Scale bars, 200 μm. (G) The number of proliferating cells in the SGZ of isoproterenol-treated mice was significantly increased compared to that in the saline-injected mice (**p<0.01). (H) A confocal section showing co-labeling of a nestin-GFP-positive cell (green) with GFAP (red) in the SGZ. Scale bar, 10 μm. (I) The percentage of cells co-expressing nestin-GFP/GFAP in the SGZ was increased in isoproterenol-vs saline-treated animals (*p<0.05).

Stimulation of β3 Adrenergic Receptors Increases Proliferation of Hippocampal Precursors In Vivo In order to determine whether similar enhancement of neural precursor activity occurs following stimulation of β3 adrenergic receptors in vivo, we injected BRL37344 directly into the hippocampus (FIG. 9A-C). A single dose of BRL37344 (0.5 µl of 10 µM) was injected directly into the hilus region on the ipsilateral side, with saline (vehicle control) being injected into the contralateral side; dividing cells were then labeled with BrdU. A significant increase in the linear density of BrdU-positive cells (expressed as number of BrdU-labeled cells per mm of SGZ) was observed in the SGZ of the BRL37344-injected hippocampus, compared to the contralateral saline-injected hippocampus (FIG. 9D-F; saline: 9.59±1.3 cells vs BRL37344: 13.36±2.0 cells; n=5; p=0.023; paired t-test). This finding demonstrates that β3 adrenergic receptor stimulation leads to proliferation of neural precursors in vivo.

We also examined the effect of systemic treatment with the β adrenergic receptor agonist isoproterenol on hippocampal neural precursor activity in mice expressing GFP under the control of nestin. Mice were treated once, daily for seven days with either saline (vehicle control) or isoproterenol, and dividing cells were again labeled with BrdU. Systemic stimulation of β adrenergic receptors resulted in a significant increase in the total number of proliferating cells in the SGZ (FIG. 9G-I; saline: 485.48±43.3 cells vs isoproterenol: 769.15±55.4 cells; n=5; p=0.0038; unpaired t-test). More interestingly, it also led to a significant increase in the percentage of nestin-GFP/GFAP double-positive cells, considered to be quiescent neural precursors (reviewed in Kempermann et. al., 2004) in the hippocampus (saline: 31.00±2.9% vs isoproterenol: 48.84±3.9%; p=0.011; unpaired t-test), confirming the activation of a latent neural precursor population in vivo.

Figure 11:
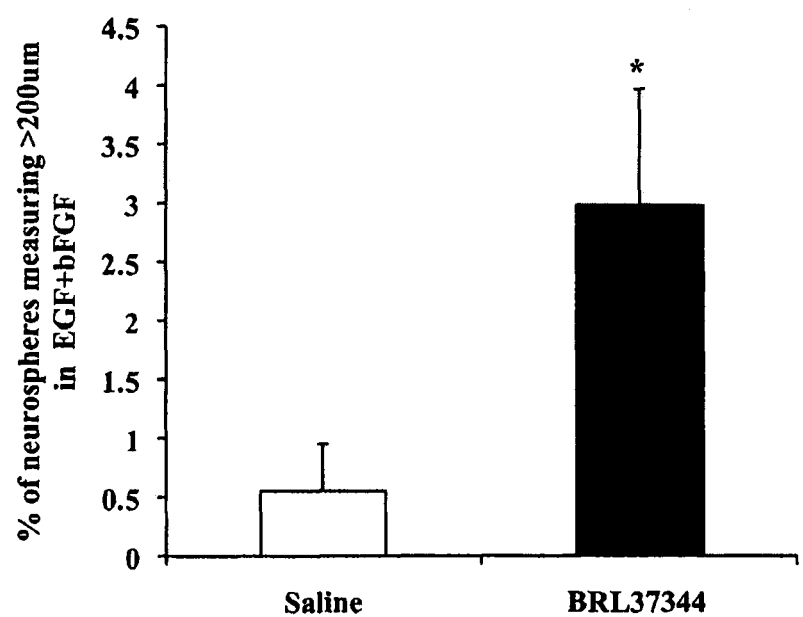
FIG. 11. Treatment of 8 weeks old C57/B16 mice with a selective β3 adrenergic receptor agonist BRL37344 (10 mg/kg; i.p.) for 7 days results in a significant activation of stem cells in the hippocampus (p=0.02; n=7) compared to those with vehicle saline. Note the increase in large neurospheres obtained in BRL37344 treated group.
Figure 12:
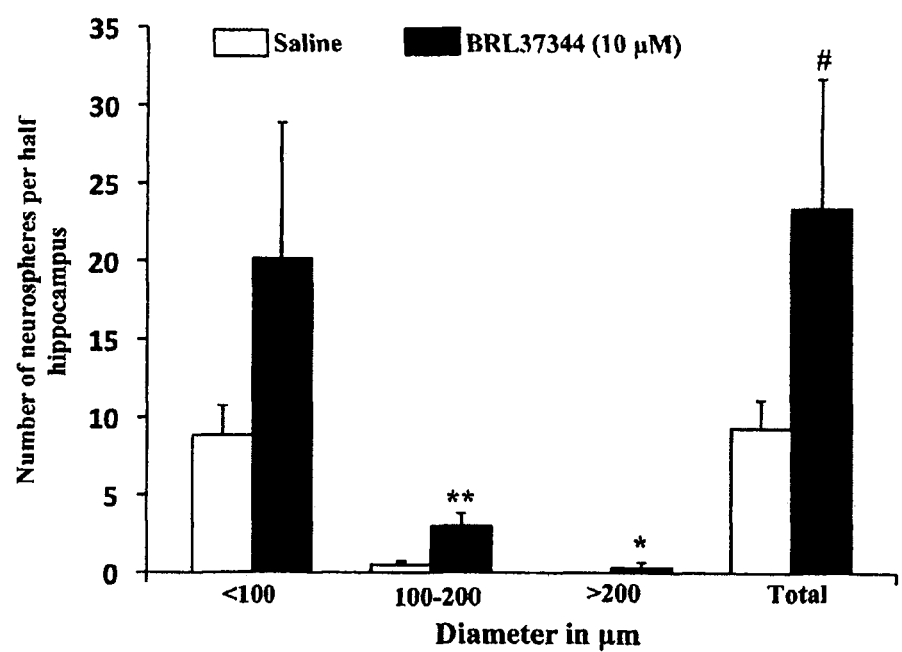
FIG. 12. Intrahippocampal infusion of BRL37344 (10 μM) for 7 days results in activation of hippocampal precursors.

Treatment of 8 weeks old C57/B16 mice with a selective β3 adrenergic receptor agonist BRL37344 (10 mg/kg; i.p.) for 7 days results in a significant activation of stem cells in the hippocampus (p=0.02; n=7) compared to those with vehicle saline. An increase in, large neurospheres obtained in BRL37344 treated group is demonstrated (FIG. 11). Intrahippocampal infusion of BRL37344 (10 µM) for 7 days results in activation of hippocampal precursors. The total number of neurospheres derived from BRL37344 treated mice (FIG. 12) is greater than when saline is infused, and the number of neurospheres with a diameter greater than 100 µM is much greater. Neurospheres with a diameter greater than 200 µM may be derived from BRL37344 treated mice.

REFERENCES

The contents of the following are incorporated herein by reference:

1. Ming, G. L. & Song, H. Adult neurogenesis in the mammalian central nervous system. Annu Rev Neurosci 28, 223-250 (2005).
2. Lledo, P. M., Alonso, M. & Grubb, M. S. Adult neurogenesis and functional plasticity in neuronal circuits. Nat Rev Neurosci 7, 179-193 (2006).
3. Ming, G.-l. & Song, H. Adult neurogenesis in the mammalian central nervous system. Annu Rev Neurosci 28, 223-250 (2005).
4. Zhao, C., Deng, W. & Gage, F. H. Mechanisms and functional implications of adult neurogenesis. Cell 132, 645-660 (2008).
5. Walker, T. L., et al. Latent stem and progenitor cells in the hippocampus are activated by neural excitation. J Neurosci 28, 5240-5247 (2008).
6. Deisseroth, K., et al. Excitation-neurogenesis coupling in adult neural stem/progenitor cells. Neuron 42, 535-552 (2004).

7. Ge, S., et al. GABA regulates synaptic integration of newly generated neurons in the adult brain. Nature 439, 589-593 (2006).
8. Tashiro, A., Sandler, V. M., Toni, N., Zhao, C. & Gage, F. H. NMDA-receptor-mediated, cell-specific integration of new neurons in adult dentate gyrus. Nature 442, 929-933 (2006).
9. Hagg, T. From neurotransmitters to neurotrophic factors to neurogenesis. Neuroscientist 15, 20-27 (200.9).
10. Vaidya, V. A., Vadodaria, K. C. & Jha, S, Neurotransmitter regulation of adult neurogenesis: putative therapeutic targets. CNS Neurol Disord Drug Targets 6, 358-374 (2007).
11. Ge, S., Pradhan, D. A., Ming, G. L. & Song, H. GABA sets the tempo for activity-dependent adult neurogenesis. Trends Neurosci 30, 1-8 (2007).
12. Nacher, J., et al. N-methyl-d-aspartate receptor expression during adult neurogenesis in the rat dentate gyrus. Neuroscience 144, 855-864 (2007).
13. Brezun, J. M. & Daszuta, A. Depletion in serotonin decreases neurogenesis in the dentate gyrus and the subventricular zone of adult rats. Neuroscience 89, 999-991002 (1999).
14. Kulkarni, V. A., Jha, S. & Vaidya, V. A. Depletion of norepinephrine decreases the proliferation, but does not influence the survival and differentiation, of granule cell progenitors in the adult rat hippocampus. Eur J Neurosci 16, 2008-2012 (2002).
15. Brezun, J. M.& Daszuta, A. Serotonergic reinnervation reverses lesion-induced decreases in PSA-NCAM labeling and proliferation of hippocampal cells in adult rats. Hippocampus 10, 37-46 (2000).
16. Malberg, J. E. & Duman, R. S. Cell proliferation in adult hippocampus is decreased by inescapable stress: reversal by fluoxetine treatment. Neuropsychopharmacology 28, 1562-1571 (2003).
17. Vollmayr, B., Mahlstedt, M. M. & Henn, F. A. Neurogenesis and depression: what animal models tell us about the link. Eur Arch Psychiatry Clin Neurosci 257, 300-303 (2007).
18. Charney, D. S. Monoamine dysfunction and the pathophysiology and treatment of depression. J Clin Psychiatry 59 Suppl 14, 11-14 (1998).
19. Malberg, J. E., Eisch, A. J., Nestler, E. J. & Duman, R. S. Chronic antidepressant treatment increases neurogenesis in adult rat hippocampus. J Neurosci 20, 9104-9110 (2000).
20. Jha, S., Rajendran, R., Davda, J. & Vaidya, V. A. Selective serotonin depletion does not regulate hippocampal neurogenesis in the adult rat brain: differential effects of p-chlorophenylalanine and 5,7-dihydroxytryptamine. Brain Res 1075, 48-59 (2006).
21. Huang, G.-J. & Herbert, J. Stimulation of neurogenesis in the hippocampus of the adult rat by fluoxetine requires rhythmic change in corticosterone. Biol Psychiatry 59, 619-624 (2006).
22. Bull, N. D. & Bartlett, P. F. The adult mouse hippocampal progenitor is neurogenic but not a stem cell. J Neurosci 25, 10815-10821 (2005).
23. Ohtsuka, T., et al. Visualization of embryonic neural stem cells using Hes promoters in transgenic mice. Mol Cell Neurosci 31, 109-122 (2006).
24. Basak, O. & Taylor, V. Identification of self-replicating multipotent progenitors in the embryonic nervous system by high Notch activity and Hes5 expression. Eur J Neurosci 25, 1006-1022 (2007).
25. Hyttel, J. Pharmacological characterization of selective serotonin reuptake inhibitors (SSRIs). Int Clin Psychopharmacol 9 Suppl 1, 19-26 (1994).
26. Kageyama, R., Ohtsuka, T., Hatakeyama, J. & Ohsawa, R. Roles of bHLH genes in neural stem cell differentiation. Exp Cell Res 306, 343-348 (2005).
27. Strosberg, A. D. Association of beta 3-adrenoceptor polymorphism with obesity and diabetes: current status. Trends Pharmacol Sci 18, 449-454 (1997).
28. Summers, R. J., Papaioannou, M., Harris, S. & Evans, B. A. Expression of beta 3-adrenoceptor mRNA in rat brain. Br J Pharmacol 116, 2547-2548 (1995).
29. Claustre, Y., et al. Effects of the beta3-adrenoceptor (Adrb3) agonist SR58611A (amibegron) on serotonergic and noradrenergic transmission in the rodent: relevance to its antidepressant/anxiolytic-like profile. Neuroscience 156, 353-364 (2008).
30. Consoli, D., Leggio, G. M., Mazzola, C., Micale, V. & Drago, F. Behavioral effects of the beta3 adrenoceptor agonist 8R58611A: is it the putative prototype of a new class of antidepressant/anxiolytic drugs? Eur J Pharmacol 573, 139-147 (2007).
31. Simiand, J., et al. Antidepressant profile in rodents of SR 58611A, a new selective agonist for atypical beta-adrenoceptors. Eur J Pharmacol 219, 193-201 (1992).
32. Stemmelin, J., et al. Stimulation of the beta3-Adrenoceptor as a novel treatment strategy for anxiety and depressive disorders. Neuropsychopharmacology 33, 574-587 (2008).
33. Gould, E. Serotonin and hippocampal neurogenesis. Neuropsychopharmacology 21, 46S-51S (1999).
34. Cryan, J. F., et al. Norepinephrine-deficient mice lack responses to antidepressant drugs, including selective serotonin reuptake inhibitors. Proc Natl Acad Sci USA 101, 8186-8191 (2004).
35. David, D. J., et al. Neurogenesis-dependent and -independent effects of fluoxetine in an animal model of anxiety/depression. Neuron 62, 479-493 (2009).
36. Wang, J. W., David, D. J., Monckton, J. E., Battaglia, F. & Hen, R. Chronic fluoxetine stimulates maturation and synaptic plasticity of adult-born hippocampal granule cells. J Neurosci 28, 1374-1384 (2008).
37. Cikos, S., et al. Expression of beta adrenergic receptors in mouse oocytes and preimplantation embryos. Mol Reprod Dev 71, 145-153 (2005).
38. Evans, B. A., Papaioannou, M., Hamilton, S. & Summers, R. J. Alternative splicing generates two isoforms of the beta3-adrenoceptor which are differentially expressed in mouse tissues. Br J Pharmacol 127, 1525-1531 (1999).
39. Greenberg, M. and Ziff, E. Nature, 311:433, 1984; eds. Burck, et al., in Oncogenes, 1988, Springer-Verlag, New York.
40. Liu et al. Journal of Biomolecular Screening 2009:319-329

The invention claimed is:

1. A method of activating a latent neural precursor cell population, comprising:
 (1) providing a neural cell population derived from the hippocampus;
 (2) introducing the neural cell population to a neurosphere-forming culture medium; and
 (3) activating the latent precursor cell population by treatment with a β3 adrenergic receptor agonist.

2. The method as claimed in claim 1 further comprising selecting cells which demonstrate the property of self-renewal and multipotency.

3. The method as claimed in claim 2 wherein neurospheres of large diameter are selected.

4. A method as claimed in claim 3 wherein neurospheres of greater than or equal to 110 mm are selected.

* * * * *